United States Patent
Hasegawa et al.

(10) Patent No.: US 6,899,990 B2
(45) Date of Patent: May 31, 2005

(54) EPOXY COMPOUND HAVING ALICYCLIC STRUCTURE, POLYMER, RESIST COMPOSITION AND PATTERNING PROCESS

(75) Inventors: Koji Hasegawa, Niigata-ken (JP); Takeshi Kinsho, Niigata-ken (JP); Takeru Watanabe, Niigata-ken (JP); Tsunehiro Nishi, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/167,393

(22) Filed: Jun. 13, 2002

(65) Prior Publication Data

US 2003/0036603 A1 Feb. 20, 2003

(30) Foreign Application Priority Data

Jun. 14, 2001 (JP) ........................................ 2001-179593

(51) Int. Cl.[7] ................................ G03F 7/00; C08F 8/00
(52) U.S. Cl. .................... 430/270.1; 430/326; 526/256; 526/268
(58) Field of Search .............................. 430/296, 270.1, 430/326; 526/256, 268

(56) References Cited

U.S. PATENT DOCUMENTS

| 6,406,828 B1 | * | 6/2002 | Szmanda et al. | ........ | 430/270.1 |
| 2002/0001772 A1 | * | 1/2002 | Nishi et al. | ............... | 430/270.1 |

FOREIGN PATENT DOCUMENTS

WO    WO-00/53658 A1 * 9/2000 ........... C08G/61/08

OTHER PUBLICATIONS

Grant et al, eds, Grant & Hackh's Chemical Dictionary, Fifth Ed, McGraw–Hill Book Company, New York, N.Y., 1987, p. 216.*
Gannon, John, "Epoxy Resins", Kirk–Othmeri Encyclopedia of Chemical Technology, 1994, John Wiley & Sons, Inc, one page, Abstract, from online version at www.mrw.interxcience.wiley,com/kirk/articles/epoxgann.a01/abstract.*

* cited by examiner

Primary Examiner—Cynthia Hamilton
(74) Attorney, Agent, or Firm—Millen, White, Zelano & Branigan, P.C.

(57) ABSTRACT

Epoxy compounds of formula (1) are provided wherein W is $CH_2$, O or S, X and Y are $—CR^1R^2—$ or $—C(=O)—$, k is 0 or 1, $R^1$ and $R^2$ are H or alkyl, or $R^1$ and $R^2$, taken together, may form an aliphatic hydrocarbon ring with the carbon atom to which they are connected. A resist composition comprising a polymer having recurring units of the epoxy compound as a base resin is sensitive to high-energy radiation, has excellent sensitivity, resolution, etching resistance, and minimized swell and lends itself to micropatterning with electron beams or deep-UV.

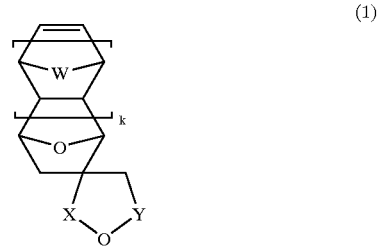

(1)

21 Claims, No Drawings

EPOXY COMPOUND HAVING ALICYCLIC STRUCTURE, POLYMER, RESIST COMPOSITION AND PATTERNING PROCESS

This invention relates to (i) a novel epoxy compound useful as a monomer to form a base resin, (ii) a polymer comprising recurring units obtained from the epoxy compound, (iii) a resist composition comprising the polymer as a base resin, especially chemically amplified resist composition adapted for micropatterning lithography, and (iv) a patterning process using the resist composition.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 $\mu$m or less.

The resist materials for use in photolithography using light of an excimer laser, especially ArF excimer laser having a wavelength of 193 nm, are, of course, required to have a high transparency to light of that wavelength. In addition, they are required to have an etching resistance sufficient to allow for film thickness reduction, a high sensitivity sufficient to eliminate any extra burden on the expensive optical material, and especially, a high resolution sufficient to form a precise micropattern. To meet these requirements, it is crucial to develop a base resin having a high transparency, rigidity and reactivity. None of the currently available polymers satisfy all of these requirements. Practically acceptable resist materials are not yet available.

Known high transparency resins include copolymers of acrylic or methacrylic acid derivatives and polymers containing in the backbone an alicyclic compound derived from a norbornene derivative. All these resins are unsatisfactory. For example, copolymers of acrylic or methacrylic acid derivatives are relatively easy to increase reactivity in that highly reactive monomers can be introduced and acid labile units can be increased as desired, but difficult to increase rigidity because of their backbone structure. On the other hand, the polymers containing an alicyclic compound in the backbone have rigidity within the acceptable range, but are less reactive with acid than poly(meth)acrylate because of their backbone structure, and difficult to increase reactivity because of the low freedom of polymerization. It is noted that the term "(meth)acrylate" is used to mean acrylate or methacrylate. Additionally, since the backbone is highly hydrophobic, these polymers are less adherent when applied to substrates. Therefore, some resist compositions which are formulated using these polymers as the base resin fail to withstand etching although they have satisfactory sensitivity and resolution. Some other resist compositions are highly resistant to etching, but have low sensitivity and low resolution below the practically acceptable level.

Both the (meth)acrylic and alicyclic backbone systems commonly have the problem of pattern disruption due to swelling of resist film. Resist compositions based on these systems have been designed so as to improve their resolution performance by increasing the difference in dissolution rate before and after exposure, and as a consequence, they eventually become highly hydrophobic. Highly hydrophobic resist compositions, when applied as a film and processed with a developer, can maintain the film tenaciously in unexposed regions and allow the film to be instantaneously dissolved in over-exposed regions, while relatively broad exposed regions therebetween allow penetration of the developer, but are kept undissolved, that is, swollen. At the very small pattern size for which ArF excimer laser is actually used, those resist compositions which allow adjacent pattern strips to be joined together and disrupted on account of swelling are rejected. While a finer pattern rule is being demanded, there is a need to have a resist material which is not only satisfactory in sensitivity, resolution, and etching resistance, but fully restrained from swelling.

SUMMARY OF THE INVENTION

An object of the invention is to provide (i) a novel epoxy compound useful as a monomer and (ii) a polymer obtained therefrom, the polymer being used in the formulation of a photoresist composition which exhibits a high transparency and substrate affinity as well as minimized swell during development when processed by photolithography using light with a wavelength of less than 300 nm, especially ArF excimer laser light as the light source. Another object is to provide (iii) a resist composition comprising the polymer as a base resin, and (iv) a patterning process using the resist composition.

The inventor has found that an epoxy compound of formula (1) can be prepared in high yields by a simple method to be described below, that a polymer obtained from the epoxy compound has a high transparency at the exposure wavelength of an excimer laser, and that a resist composition comprising the polymer as a base resin is improved in resolution, substrate adhesion and swell suppression during development.

In a first aspect, the invention provides an epoxy compound having the following general formula (1).

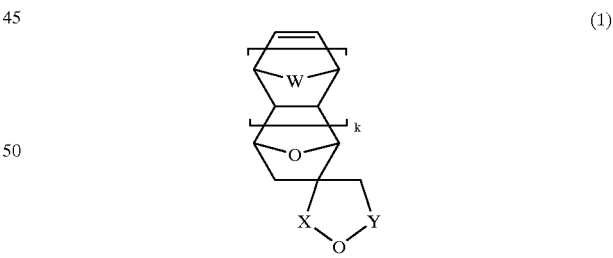

(1)

Herein, W is $CH_2$, an oxygen atom or sulfur atom, X and Y are independently $—CR^1R^2—$ or $—C(=O)—$, k is 0 or 1, $R^1$ and $R^2$ are independently hydrogen or straight, branched or cyclic alkyl groups of 1 to 10 carbon atoms in which some or all of the hydrogen atoms on constituent carbon atoms may be substituted with halogen atoms, or $R^1$ and $R^2$, taken together, may form an aliphatic hydrocarbon ring with the carbon atom to which they are connected.

The preferred epoxy compound has the following general formula (2).

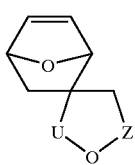

(2)

Herein, one of U and Z is —CR³R⁴— or —C(=O)—, the other is CH₂, R³ and R⁴ are independently hydrogen or straight, branched or cyclic alkyl groups of 1 to 6 carbon atoms, or R³ and R⁴, taken together, may form an aliphatic hydrocarbon ring with the carbon atom to which they are connected.

In a second aspect, the invention provides a polymer comprising recurring units obtained from the epoxy compound of the formula (1) or (2).

In a third aspect, the invention provides a resist composition comprising the above polymer as a base resin.

In a fourth aspect, the invention provides a process for forming a resist pattern comprising the steps of applying the above resist composition onto a substrate to form a coating; heat treating the coating and then exposing it to high-energy radiation or electron beam through a photo mask; and optionally heat treating the exposed coating and developing it with a developer.

DESCRIPTION OF THE PREFERRED EMBODIMENTS

Epoxy Compound

The epoxy compounds of the invention have the following general formula (1).

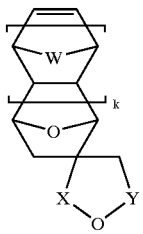

(1)

Herein W is CH₂, an oxygen atom or sulfur atom, X and Y each are independently —CR¹R²— or —C(=O)—, and k is 0 or 1. R¹ and R² each are independently hydrogen or straight, branched or cyclic alkyl groups of 1 to 10 carbon atoms in which some or all of the hydrogen atoms on constituent carbon atoms may be substituted with halogen atoms. Examples of substituted or unsubstituted alkyl groups include methyl, ethyl, n-propyl, isopropyl, n-butyl, sec-butyl, tert-butyl, tert-amyl, n-pentyl, n-hexyl, cyclopentyl, cyclohexyl, bicyclo[2.2.1]heptyl, bicyclo[2.2.2]octyl, bicyclo[3.3.1]nonyl, bicyclo[4.4.0]decanyl, adamantyl, trifluoromethyl, 2,2,2-trifluoroethyl, 2,2,2-trichloroethyl, 3,3,3-trifluoropropyl and 3,3,3-trichloropropyl. Alternatively, R¹ and R², taken together, may form an aliphatic hydrocarbon ring with the carbon atom to which they are connected. Illustrative of the ring thus formed are cyclopropane, cyclobutane, cyclopentane, cyclohexane, bicyclo[2.2.1]heptane, bicyclo[2.2.2]octane, bicyclo[3.3.1]nonane, bicyclo[4.4.0]decane, and adamantane.

Of the epoxy compounds of formula (1), those epoxy compounds having the following general formula (2) are preferred.

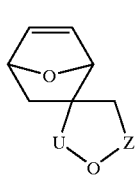

(2)

Herein one of U and Z is —CR³R⁴— or —C(=O)—, and the other is CH₂. R³ and R⁴ each are independently hydrogen or straight, branched or cyclic alkyl groups of 1 to 6 carbon atoms, for example, such as methyl, ethyl, n-propyl, isopropyl, n-butyl, sec-butyl, tert-butyl, tert-amyl, n-pentyl, n-hexyl, cyclopentyl, and cyclohexyl. Alternatively, R³ and R⁴, taken together, may form an aliphatic hydrocarbon ring with the carbon atom to which they are connected. Illustrative of the ring thus formed are cyclopropane, cyclobutane, cyclopentane, and cyclohexane.

Illustrative, non-limiting, examples of the epoxy compounds of formulas (1) and (2) are given below.

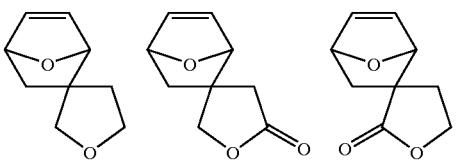

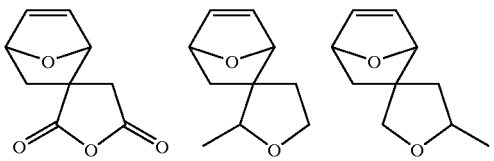

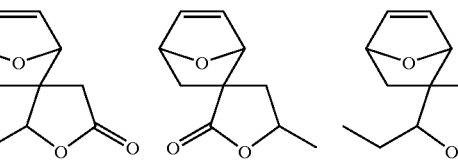

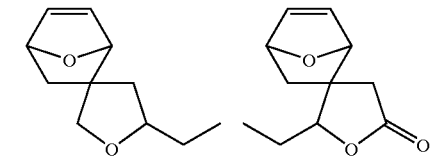

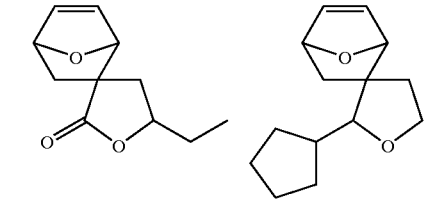

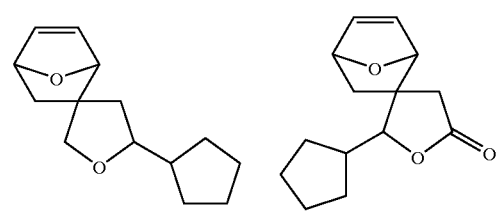
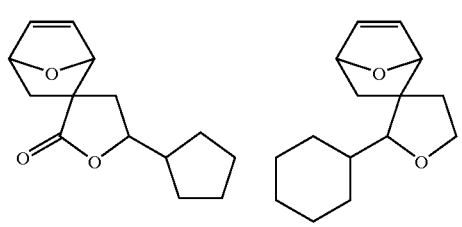
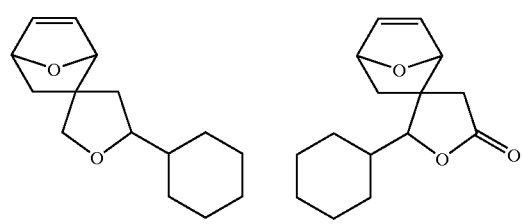
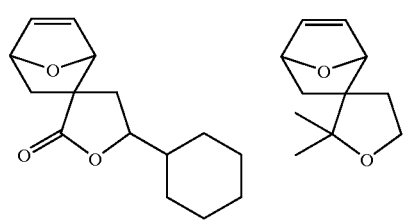
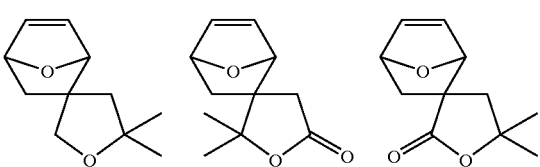
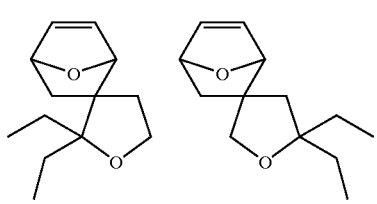
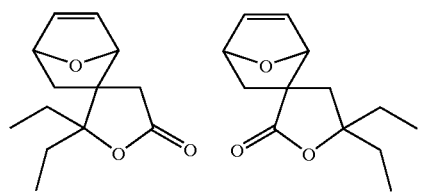
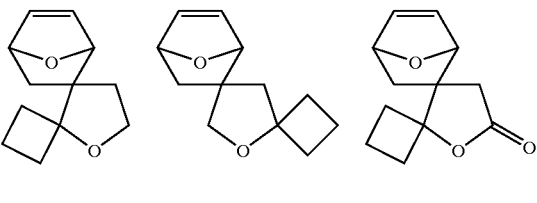
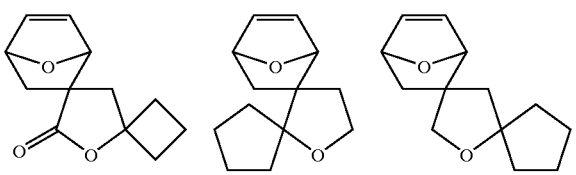
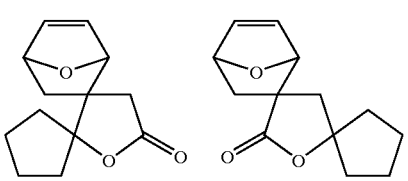
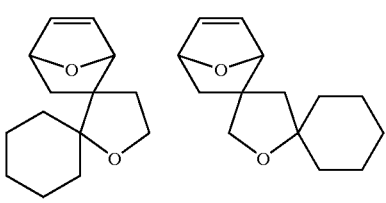
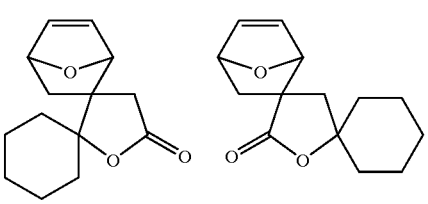
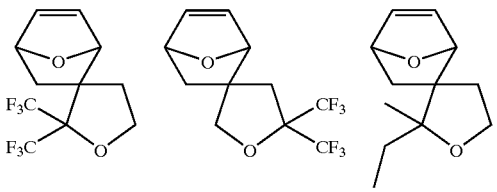
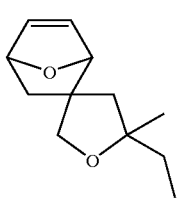

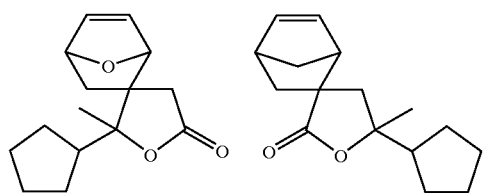
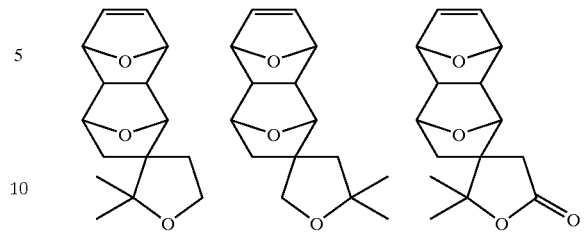
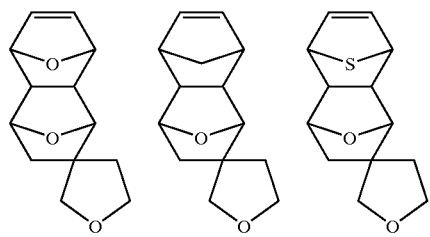
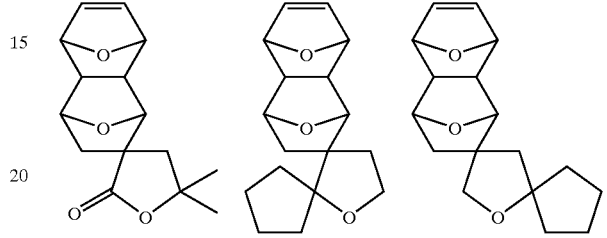
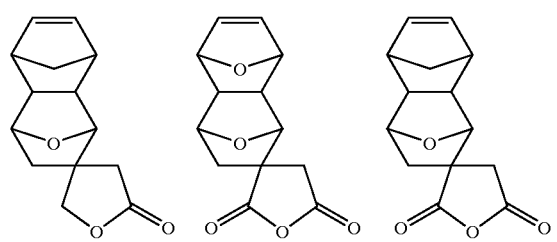
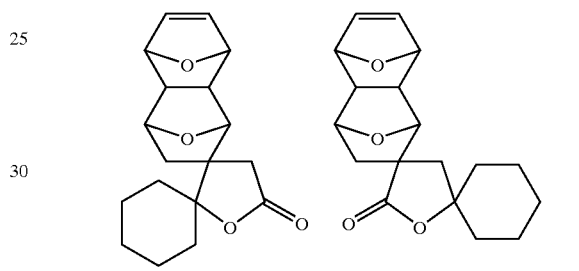
The epoxy compound of the invention can be prepared as shown by the following reaction scheme, for example, although the preparation process is not limited thereto. Processes i) to iii) in the reaction scheme are described in detail.
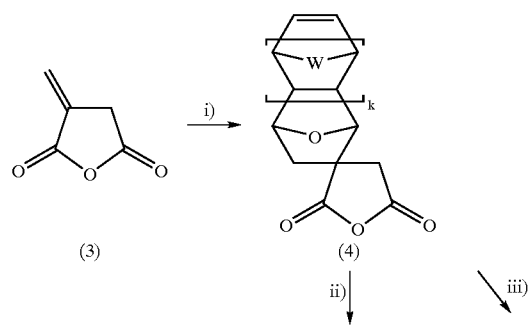

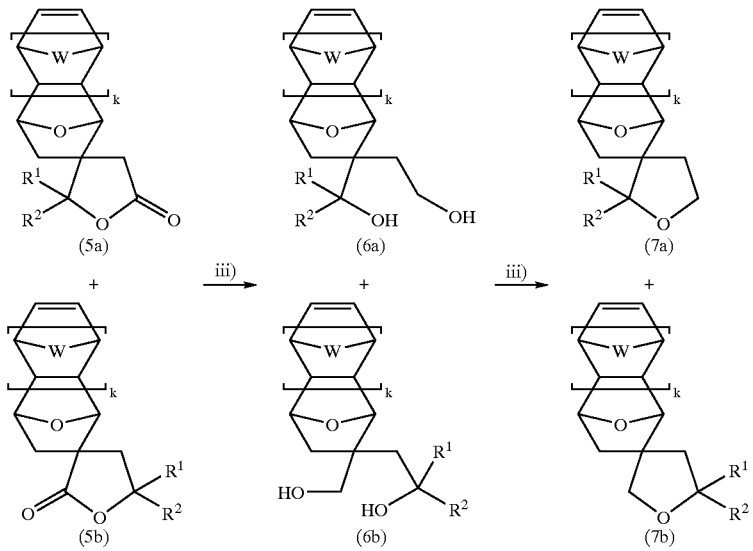

Note that $R^1$, $R^2$, W and k are as defined above.

i) A first process intends to produce an epoxy compound of formula (1) wherein both X and Y are —C(=O)—. Specifically, itaconic anhydride (3) and a corresponding diene undergo Diels-Alder reaction to form a desired epoxy compound (4). In an example where the diene used is furan, 1 to 10 moles of furan is used per mole of itaconic anhydride (3), and reaction is preferably effected at a temperature in the range of 10 to 100° C., preferably 20 to 50° C. and for a time in the range of about 5 to 100 hours, preferably about 10 to 48 hours, because higher yields are achieved. To increase the reaction rate, a Lewis acid may be added, for example, lithium chloride, aluminum chloride, zinc chloride, zinc iodide, titanium tetrachloride and boron trifluoride.

ii) A second process is to produce an epoxy compound of formula (1) wherein one of X and Y is —$CR^1R^2$— and the other is —C(=O)—. Specifically, the acid anhydride (4) undergoes reducing reaction or nucleophilic addition reaction with an organometallic reagent to produce desired epoxy compounds (5a) and (5b).

Where $R^1$ and $R^2$ are hydrogen, the process is reduction reaction on a carbonyl group of the acid anhydride (4). Examples of the reducing agent used herein include complex hydrides such as sodium boron hydride, lithium boron hydride, potassium boron hydride, calcium boron hydride, sodium aluminum hydride, lithium aluminum hydride, lithium triethylboron hydride, lithium tri-s-butylboron hydride, and potassium tri-s-butylboron hydride, and alkoxy or alkyl derivatives thereof. An appropriate amount of the reducing agent used is 0.3 to 4.0 moles, especially 0.5 to 2.0 moles per mole of the acid anhydride (4). A solvent may be used. Exemplary solvents include water, ethers such as tetrahydrofuran, diethyl ether, di-n-butyl ether and 1,4-dioxane, hydrocarbons such as n-hexane, n-heptane, benzene, toluene, xylene and cumene, alcohols such as methanol, ethanol, isopropyl alcohol and tert-butyl alcohol, and aprotic polar solvents such as dimethyl sulfoxide (DMSO), N,N-dimethylformamide (DMF) and acetonitrile, which may be used alone or in admixture. The reaction temperature and time vary over a wide range depending on other reaction parameters. Where sodium boron hydride is used as the reducing agent, for example, reaction is carried out at a temperature of −20° C. to 50° C., and preferably −10° C. to 20° C. The reaction time is desirably determined by monitoring the reaction until the completion by gas chromatography (GC) or silica gel thin-layer chromatography (TLC) because higher yields are expectable. The reaction time is usually about 0.5 to about 5 hours. From the reaction mixture, the end epoxy compounds (5a) and (5b) are obtained by a conventional aqueous work-up step. If necessary, the end compounds are purified by any conventional technique such as distillation or chromatography.

Where $R^1$ and $R^2$ are alkyl groups, the process is nucleophilic addition reaction of the acid anhydride (4) with organometallic reagents (8) and (9) to produce hydroxycarboxylic acid compounds (10a) and (10b), which are, in turn, lactonized to produce desired epoxy compounds (5a) and (5b) as shown below.

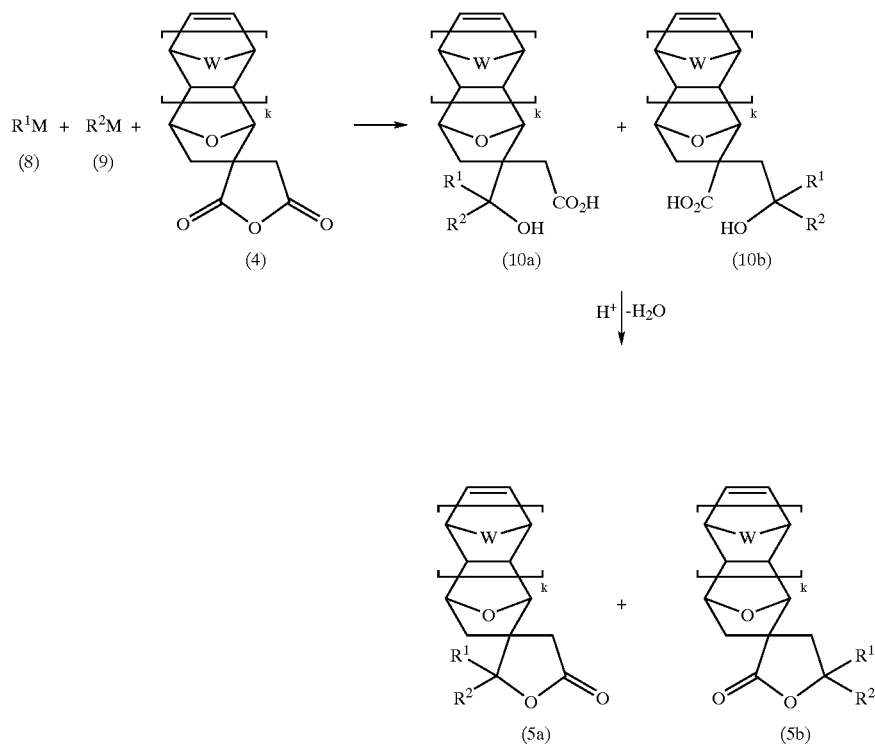

Herein, $R^1$, $R^2$, W and k are as defined above; M is Li, Na, K, MgP or ZnP, and P is a halogen atom.

The first step is nucleophilic addition reaction of organometallic reagents (8) and (9) to acid anhydride (4) to produce hydroxycarboxylic acid compounds (10a) and (10b). An appropriate amount of the organometallic reagents (8) and (9) used is 2.0 to 5.0 moles, especially 2.0 to 3.0 moles per mole of the acid anhydride (4). A solvent may be used. Preferred solvents include ethers such as tetrahydrofuran, diethyl ether, di-n-butyl ether and 1,4-dioxane, and hydrocarbons such as n-hexane, n-heptane, benzene, toluene, xylene and cumene, which may be used alone or in admixture. The reaction temperature and time vary over a wide range depending on other reaction parameters. Where Grignard reagents (of formulae (8) and (9) wherein M is MgP) are used as the organometallic reagents, for example, reaction is carried out at a temperature of −20° C. to 100° C., and preferably 0° C. to 50° C. The reaction time is desirably determined by monitoring the reaction until the completion by gas chromatography (GC) or silica gel thin-layer chromatography (TLC) because higher yields are expectable. The reaction time is usually about 0.5 to about 5 hours. From the reaction mixture, the hydroxycarboxylic acid compounds (10a) and (10b) are obtained by a conventional aqueous work-up step. If necessary, the compounds are purified by any conventional technique such as distillation or chromatography.

The second step is lactonization (or dehydration condensation) of the hydroxycarboxylic acid compounds (10a) and (10b) under acidic conditions to produce the end epoxy compounds (5a) and (5b). Preferred examples of the acid catalyst used herein include inorganic acids such as hydrochloric acid, hydrobromic acid, sulfuric acid and nitric acid and organic acids such as formic acid, acetic acid, oxalic acid, p-toluenesulfonic acid, and benzenesulfonic acid. An appropriate amount of the acid catalyst used is 0.01 to 10 moles, and preferably 0.1 to 0.5 mole per mole of the hydroxycarboxylic acid compounds (10a) and (10b). To remove water which forms with the progress of reaction, a hydrocarbon such as n-hexane, n-heptane, benzene, toluene, xylene or cumene is used as the solvent in the reaction system. Then by positively azeotroping off water from the system, reaction can be accelerated.

iii) A third process is to produce an epoxy compound of formula (1) wherein one of X and Y is —$CR^1R^2$— and the other is —$CH_2$—. Specifically, the epoxy compound resulting from process i) or ii) is subjected to reducing reaction to produce diol compounds (6a) and (6b) which are, in turn, etherified to produce desired epoxy compounds (7a) and (7b).

The first step is reducing reaction of the epoxy compound resulting from process i) or ii) to produce diol compounds (6a) and (6b). For this reaction, the same procedure as used in the step of converting acid anhydride (4) to end epoxy compounds (5a) and (5b), described above for process ii) is applicable. For example, where the epoxy compounds (5a) and (5b) are reduced with lithium aluminum hydride in tetrahydrofuran, it is recommended to use 0.5 to 1.0 mole of the reducing agent per mole of the epoxy compounds (5a) and (5b) and to conduct reaction at a temperature of 0 to 20° C. for a time of about 0.5 to 3 hours. From the reaction mixture, the intermediate diol compounds (6a) and (6b) are obtained by a conventional aqueous work-up step. If necessary, the compounds are purified by any conventional technique such as distillation or chromatography.

The second step is etherification (or intramolecular cyclization) of the diol compounds (6a) and (6b) to produce the end epoxy compounds (7a) and (7b) as shown below.

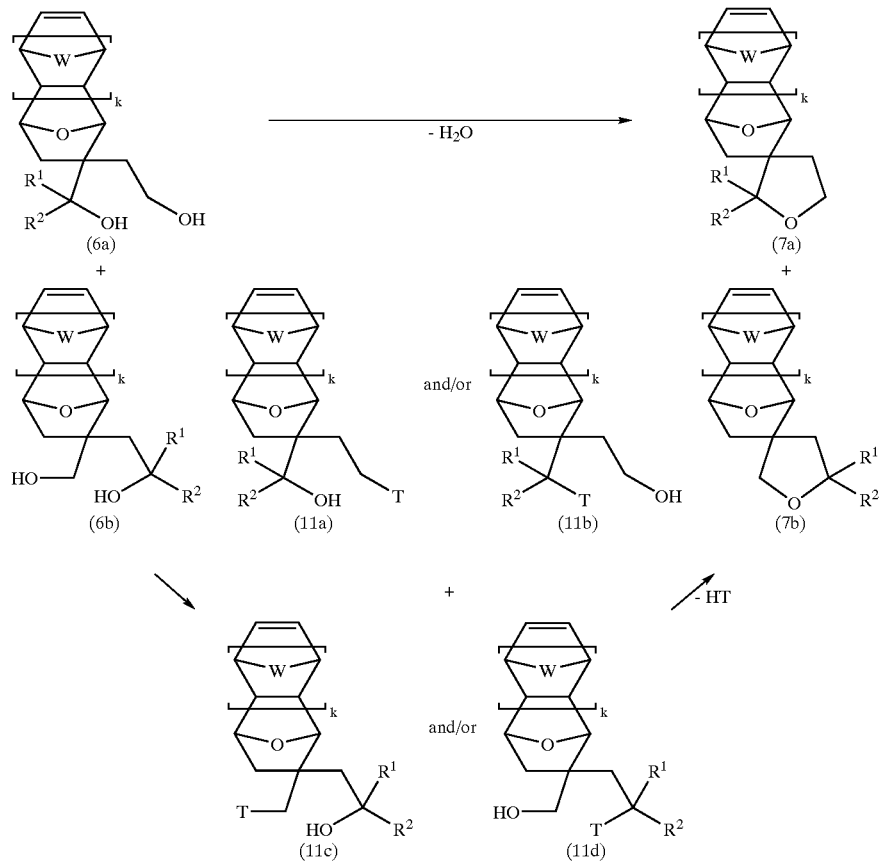

Herein, $R^1$, $R^2$, W and k are as defined above; T is a halogen atom, alkylsulfonyloxy or arylsulfonyloxy group.

A first etherification method is intramolecular dehydrating cyclization of the diol compounds (6a) and (6b). Better results are obtained when this intramolecular dehydrating reaction is carried out using an acid or salt thereof or a phosphorus reagent.

Examples of the acid used herein include inorganic acids such as hydrochloric acid, hydrobromic acid, sulfuric acid, nitric acid, perchloric acid, and phosphoric acid and organic acids such as formic acid, acetic acid, oxalic acid, benzoic acid, p-toluenesulfonic acid, and benzenesulfonic acid, and salts thereof as well as cation-exchange resins. The amount of acid used is a catalytic amount, preferably 0.01 to 10 moles, especially 0.01 to 0.5 mole per mole of the diol compounds (6a) and (6b). To remove the water formed with the progress of reaction, it is recommended that the water be positively removed from the system by azeotropic distillation using a hydrocarbon such as n-hexane, n-heptane, benzene, toluene, xylene or cumene, for thereby accelerating the reaction. Also, the reaction may be carried out in vacuum.

Examples of the phosphorus reagent include hexamethylphosphoric triamide (HMPA), dialkyl azodicarboxylate-triphenylphosphine, triethylphosphine, and potassium carbonate-triphenylphosphine. The amount of phosphorus reagent used is preferably 0.9 to 10 moles, especially 1.0 to 1.2 moles per mole of the diol compound (6a) and (6b).

The reaction temperature and time vary with other conditions. In one example using triphenylsphosphine and carbon tetrachloride, the reaction temperature is room temperature to the reflux temperature, desirably 50° C. to the reflux temperature for rapidly driving the reaction to completion. The reaction time is desirably determined by monitoring the reaction until the completion by gas chromatography (GC) or silica gel thin-layer chromatography (TLC) because higher yields are expectable. The reaction time is usually about 1 to about 30 hours. From the reaction mixture, the end epoxy compounds (7a) and (7b) are obtained by a conventional aqueous work-up step. If necessary, the end compounds are purified by any conventional technique such as distillation or chromatography.

A second etherification method involves the steps of converting the diol compounds (6a) and (6b) to compounds (11a) to (11d) having an eliminatable group such as halogen, and treating these compounds with a base for cyclization into epoxy compounds (7a) and (7b).

The first step is to synthesize the compounds (11a) to (11d) having an eliminatable group. The compounds (6a) and (6b) each have within the molecule two hydroxyl groups, only one of which is converted to an eliminatable group T. When at least one of $R^1$ and $R^2$ is not hydrogen, one of the two hydroxyl groups is a primary hydroxyl group and the other is a secondary or tertiary hydroxyl group. It is then relatively easy to convert only one hydroxyl group to an eliminatable group T by utilizing a difference in reactivity between the two. In contrast, when both $R^1$ and $R^2$ are hydrogen, the two hydroxyl groups are both primary. Then the amounts of reagents and reaction conditions must be carefully determined in order to convert only one hydroxyl group to an eliminatable group T.

In the case of the compounds (11a) to (11d) having an eliminatable group T which is a halogen atom, T is preferably chlorine or bromine. In this case, various well-known methods are applicable to the synthesis of haloalcohol compounds (11a) to (11d) from diol compounds (6a) and (6b). Some exemplary methods use hydrohalogenic acids such as hydrochloric acid and hydrobromic acid, sulfur reagents such as thionyl chloride and thionyl bromide, and phosphorus reagents such as phosphorus trichloride, phosphorus pentachloride, phosphorus tribromide or triphenylphosphine combined with various halogen sources.

The reaction temperature and time largely vary with reagents and conditions. In one example wherein a Vilsmeier reagent is prepared using phosphorus pentachloride in dimethylformamide (DMF) and reacted in situ to chlorinate one primary hydroxyl group, a temperature in the range of −20° C. to room temperature, desirably 0° C. to room temperature is preferred for high selectivity of reaction. The reaction time is desirably determined by monitoring the reaction until the completion by gas chromatography (GC) or silica gel thin-layer chromatography (TLC) because higher yields are expectable. The reaction time is usually about 1 to about 50 hours.

From the reaction mixture, the end haloalcohol compounds (11a) to (11d) are obtained by a conventional aqueous work-up step. If necessary, the compounds are purified by any conventional technique such as distillation, chromatography or recrystallization. In most cases, the crude product has such a purity that it may be used in the subsequent step without purification.

In the case of the compounds (11a) to (11d) having an eliminatable group T which is an alkylsulfonyloxy or arylsulfonyloxy group, T is preferably a methanesulfonyloxy, trifluoromethanesulfonyloxy, benzenesulfonyloxy or p-toluenesulfonyloxy group for availability of their starting materials. In this case, the sulfonyloxy compounds (11a) to (11d) are conventionally synthesized by reacting a corresponding sulfonyl halide with the diol compounds (6a) and (6b) in a solvent in the presence of a base.

The sulfonyl halide is exemplified by methanesulfonyl chloride, trifluoromethanesulfonyl chloride, benzenesulfonyl chloride and p-toluenesulfonyl chloride. An appropriate amount of the sulfonyl halide used is 0.9 to 10 moles, especially 1.0 to 1.2 moles per mole of the diol compounds (6a) and (6b) in order to convert only one of the hydroxyl groups on the diol compounds (6a) and (6b) to an eliminatable group T.

Examples of the base used herein include organic amines such as pyridine, triethylamine, N,N-dimethylaniline and 4-dimethylaminopyridine; alkoxides such as sodium methoxide, sodium ethoxide, lithium methoxide, lithium ethoxide, lithium tert-butoxide and potassium tert-butoxide; inorganic hydroxides such as sodium hydroxide, lithium hydroxide, potassium hydroxide, barium hydroxide and tetra-n-butylammonium hydroxide; inorganic carbonates such as sodium carbonate, sodium hydrogen carbonate, lithium carbonate and potassium carbonate; and metal amides such as sodium amide, potassium amide, lithium diisopropylamide, potassium diisopropylamide, lithium dicyclohexylamide, potassium dicyclohexylamide, lithium 2,2,6,6-tetramethylpiperidine, lithium bistrimethylsilylamide, sodium bistrimethylsilylamide, potassium bistrimethylsilylamide, lithium isopropylcyclohexylamide and bromomagnesium diisopropylamide. An appropriate amount of the base used is 0.9 to 100 moles, especially 1.0 to 100 moles per mole of the diol compounds (6a) and (6b). The base itself may also be used as a solvent.

Suitable solvents include ethers such as tetrahydrofuran, diethyl ether and di-n-butyl ether; chlorinated organic solvents such as methylene chloride and chloroform; hydrocarbons such as n-hexane, n-heptane, benzene, toluene, xylene and cumene; and aprotic polar solvents such as dimethyl sulfoxide (DMSO) and N,N-dimethylforamide (DMF). Depending on reaction conditions, a choice may be made among these solvents and mixtures thereof.

The reaction temperature and time largely vary with reagents and conditions. In one example wherein mono-p-toluene sulfonate is synthesized using p-toluenesulfonyl chloride and pyridine as the base and solvent, a temperature in the range of −20° C. to room temperature, desirably 0° C. to room temperature is preferred for the completion of reaction and the high purity of the reaction product. The reaction time is desirably determined by monitoring the reaction until the completion by gas chromatography (GC) or silica gel thin-layer chromatography (TLC) because higher yields are expectable. The reaction time is usually about 1 to about 60 hours.

From the reaction mixture, the end sulfonyloxy compounds (11a) to (11d) are obtained by a conventional aqueous work-up step. If necessary, the compounds are purified by any conventional technique such as distillation, chromatography or recrystallization. In most cases, the crude product has such a purity that it may be used in the subsequent step without purification.

In a further embodiment, the compounds (11a) to (11d) in which T is an alkylsulfonyloxy or arylsulfonyloxy group can be converted to the haloalcohol compounds (11a) to (11d) in which T is halogen. In this embodiment, reaction may be performed in a polar solvent such as dimethylformamide (DMF), dimethyl sulfoxide (DMSO) or ethanol at an elevated temperature in the range of room temperature to the reflux temperature of the solvent, using a halide salt such as lithium chloride, lithium bromide, sodium bromide or calcium bromide in more than stoichiometric amounts.

In the second step, a base acts on the compounds (11a) to (11d) having an eliminatable group in a solvent to produce the end epoxy compounds (7a) and (7b). Examples of the base used herein include alkoxides such as sodium methoxide, sodium ethoxide, lithium methoxide, lithium ethoxide, lithium tert-butoxide and potassium tert-butoxide; organic amines such as pyridine, triethylamine, N,N-dimethylaniline and 4-dimethylaminopyridine; inorganic hydroxides such as sodium hydroxide, lithium hydroxide, potassium hydroxide, barium hydroxide and tetra-n-butylammonium hydroxide; inorganic carbonates such as sodium carbonate, sodium hydrogen carbonate, lithium carbonate and potassium carbonate; alkyl metal compounds such as trityllithium, tritylsodium, tritylpotassium, methyllithium, phenyllithium, sec-butyllithium, tert-butyllithium and ethyl magnesium bromide; and metal amides such as sodium amide, potassium amide, lithium diisopropylamide, potassium diisopropylamide, lithium dicyclohexylamide, potassium dicyclohexylamide, lithium 2,2,6,6-tetramethylpiperidine, lithium bistrimethylsilylamide, sodium bistrimethylsilylamide, potassium bistrimethylsilylamide, lithium isopropylcyclohexylamide and bromomagnesium diisopropylamide. In the event where compounds (11a) to (11d) having an eliminatable group is synthesized in the first step using a base, it can be further converted to epoxy compounds (7a) and (7b) without any additional measure. An appropriate amount of the base used is 0.9 to 100 moles, especially 1.0 to 100 moles per mole of the compounds (11a) to (11d) having an eliminatable group.

Suitable solvents include water, ethers such as tetrahydrofuran, diethyl ether, di-n-butyl ether and 1,4-dioxane; hydrocarbons such as n-hexane, n-heptane, benzene, toluene, xylene and cumene; alcohols such as methanol, ethanol, isopropyl alcohol and tert-butyl alcohol; aprotic polar solvents such as dimethyl sulfoxide (DMSO) and N,N-dimethylforamide (DMF); and chlorinated organic solvents such as methylene chloride, chloroform and carbon tetrachloride. Depending on reaction conditions, a choice may be made among these solvents and mixtures thereof. The base itself may be used as the solvent.

The reaction temperature and time largely vary with reagents and conditions. In one example wherein cyclization reaction is performed under two-layer conditions using an aqueous sodium hydroxide solution and toluene, a temperature in the range of room temperature to 100° C., desirably 50 to 100° C. is preferred for the quick completion of reaction. The reaction time is desirably determined by monitoring the reaction until the completion by gas chromatography (GC) or silica gel thin-layer chromatography (TLC) because higher yields are expectable. The reaction time is usually about 1 to about 60 hours.

From the reaction mixture, the end epoxy compounds (7a) and (7b) are obtained by a conventional aqueous work-up step. If necessary, the compounds are purified by any conventional technique such as distillation or chromatography.

Polymer

The polymer or high molecular weight compound of the invention is characterized by comprising recurring units obtained from the epoxy compound of formula (1).

Illustratively, the recurring units obtained from the epoxy compound of formula (1) are those of the following formulae (1a) and (1b) wherein W, X, Y and k are as defined above.

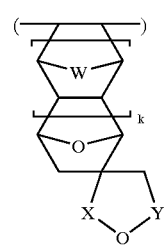

(1a)

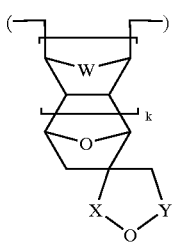

(2a)

In addition to the recurring units of formulae (1a) and (2a), the polymer of the invention may further include recurring units obtained from another monomer having a polymerizable double bond.

Illustrative examples of the recurring units obtained from another monomer having a polymerizable double bond are those of the general formulae (M1) to (M16) below.

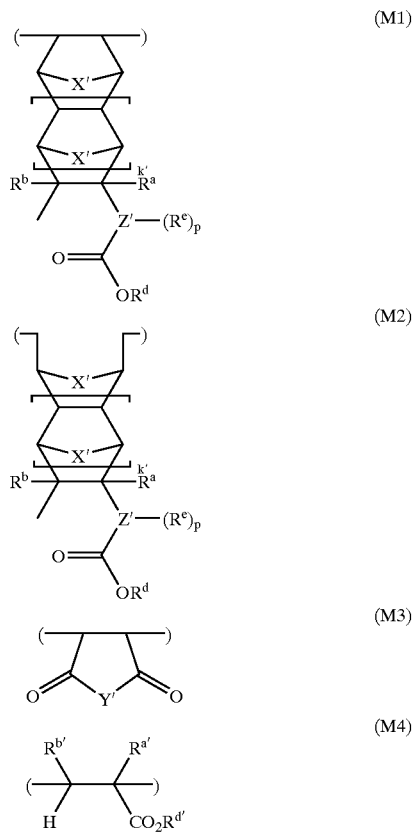

Herein $R^a$ and $R^{a'}$ each are hydrogen, methyl or $CH_2CO_2R^c$, $R^b$ and $R^{b'}$ each are hydrogen, methyl or $CO_2R^c$, $R^c$ which may be identical or different between $R^a$ and $R^{a'}$ and between $R^b$ and $R^{b'}$ is a straight, branched or cyclic alkyl group of 1 to 15 carbon atoms, $R^d$ and $R^{d'}$ each are an acid labile group, $R^e$ is a halogen atom, a hydroxyl group, a straight, branched or cyclic alkoxy, acyloxy or alkylsulfonyloxy group having 1 to 15 carbon atoms, or a straight, branched or cyclic alkoxycarbonyloxy or alkoxyalkoxy group having 2 to 15 carbon atoms, in which some or all of the hydrogen atoms on constituent carbon atoms may be substituted with halogen atoms, X' is $CH_2$, an oxygen or sulfur atom, Y' is —O— or —(NR$^f$)— wherein R$^f$ is hydrogen or a straight, branched or cyclic alkyl group of 1 to 15 carbon atoms, Z' is a single bond or a straight, branched or cyclic (p+2)-valent hydrocarbon group having 1 to 5 carbon atoms, in which at least one methylene group may be substituted with an oxygen atom to form a chain-like or cyclic ether or two hydrogen atoms on a common carbon may be substituted with an oxygen atom to form a ketone, k' is 0 or 1, p is 0, 1 or 2.

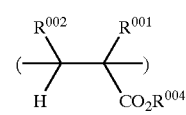

(M5)

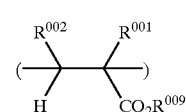

(M6)

-continued

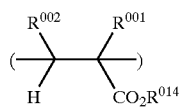

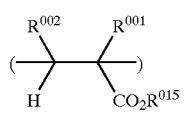

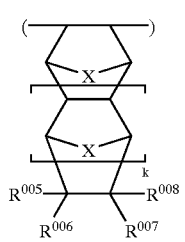

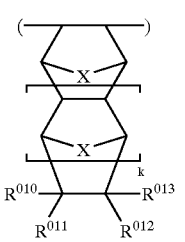

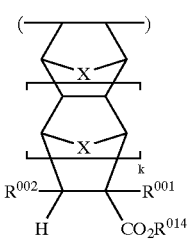

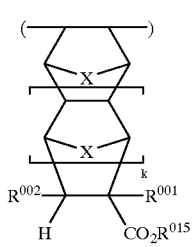

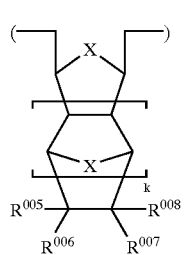

(M7)

(M8)

(M9)

(M10)

(M11)

(M12)

(M13)

-continued

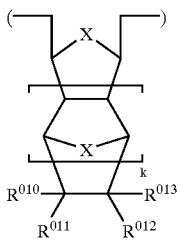 (M14)

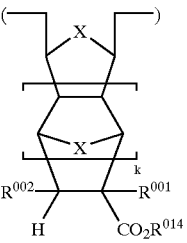 (M15)

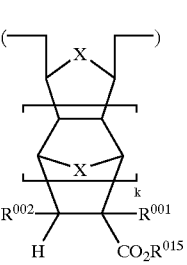 (M16)

Herein, $R^{001}$ is hydrogen, methyl or $CH_2CO_2R^{003}$. $R^{002}$ is hydrogen, methyl or $CO_2R^{003}$. $R^{003}$ is a straight, branched or cyclic alkyl group of 1 to 15 carbon atoms. $R^{004}$ is hydrogen or a monovalent hydrocarbon group of 1 to 15 carbon atoms having a carboxyl or hydroxyl group. At least one of $R^{005}$ to $R^{008}$ represents a monovalent hydrocarbon group of 1 to 15 carbon atoms having a carboxyl or hydroxyl group while the remaining R's independently represent hydrogen or a straight, branched or cyclic alkyl group of 1 to 15 carbon atoms. Alternatively, $R^{005}$ to $R^{008}$, taken together, may form a ring, and in that event, at least one of $R^{005}$ to $R^{008}$ is a divalent hydrocarbon group of 1 to 15 carbon atoms having a carboxyl or hydroxyl group, while the remaining R's are independently single bonds or straight, branched or cyclic alkylene groups of 1 to 15 carbon atoms. $R^{009}$ is a monovalent hydrocarbon group of 2 to 15 carbon atoms containing at least one partial structure selected from among ether, aldehyde, ketone, ester, carbonate, acid anhydride, amide and imide. At least one of $R^{010}$ to $R^{013}$ is a monovalent hydrocarbon group of 2 to 15 carbon atoms containing at least one partial structure selected from among ether, aldehyde, ketone, ester, carbonate, acid anhydride, amide and imide, while the remaining R's are independently hydrogen or straight, branched or cyclic alkyl groups of 1 to 15 carbon atoms. $R^{010}$ to $R^{013}$, taken together, may form a ring, and in that event, at least one of $R^{010}$ to $R^{013}$ is a divalent hydrocarbon group of 1 to 15 carbon atoms containing at least one partial structure selected from among ether, aldehyde, ketone, ester, carbonate, acid anhydride, amide and imide, while the remaining R's are independently single bonds or straight, branched or cyclic alkylene groups of 1 to 15 carbon atoms. $R^{O14}$ is a polycyclic hydrocarbon group having 7 to 15 carbon atoms or an alkyl group containing a polycyclic hydrocarbon group. $R^{O15}$ is an acid labile group. X is $CH_2$ or an oxygen atom. Letter k is equal to 0 or 1.

More illustratively, $R^a$ and $R^{a'}$ are independently hydrogen, methyl or $CH_2CO_2R^c$. $R^b$ and $R^{b'}$ are independently hydrogen, methyl or $CO_2R^c$. $R^c$ may be identical or different between $R^a$ and $R^{a'}$ and between $R^b$ and $R^{b'}$ and is a straight, branched or cyclic alkyl group of 1 to 15 carbon atoms, for example, methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, and butyladamantyl. $R^d$ and $R^{d'}$ are independently acid labile groups which will be described later in detail. $R^e$ is a halogen atom, a hydroxyl group, a straight, branched or cyclic alkoxy, acyloxy or alkylsulfonyloxy group having 1 to 15 carbon atoms, or a straight, branched or cyclic alkoxycarbonyloxy or alkoxyalkoxy group having 2 to 15 carbon atoms, in which some or all of the hydrogen atoms on constituent carbon atoms may be substituted with halogen atoms. Exemplary of $R^e$ are fluoro, chloro, bromo, hydroxyl, methoxy, ethoxy, propoxy, isopropoxy, n-butoxy, sec-butoxy, tert-butoxy, tert-amyloxy, n-pentoxy, n-hexyloxy, cyclopentyloxy, cyclohexyloxy, ethylcyclopentyloxy, butylcyclopentyloxy, ethylcyclohexyloxy, butylcyclohexyloxy, adamantyloxy, ethyladamantyloxy, butyladamantyloxy, formyloxy, acetoxy, ethylcarbonyloxy, pivaloyloxy, methanesulfonyloxy, ethanesulfonyloxy, n-butanesulfonyloxy, trifluoroacetoxy, trichloroacetoxy, 3,3,3-trifluoroethylcarbonyloxy, methoxymethoxy, 1-ethoxyethoxy, 1-ethoxypropoxy, 1-tert-butoxyethoxy, 1-cyclohexyloxyethoxy, 2-tetrahydrofuranyloxy, 2-tetrahydropyranyloxy, methoxycarbonyloxy, ethoxycarbonyloxy, and tert-butoxycarbonyloxy. X' is $CH_2$, an oxygen or sulfur atom. Y' is —O— or —($NR^f$)— wherein $R^f$ is hydrogen or a straight, branched or cyclic alkyl group of 1 to 15 carbon atoms, for example, methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, and butyladamantyl. Z' is a single bond or a straight, branched or cyclic (p+2)-valent hydrocarbon group having 1 to 5 carbon atoms, in which at least one methylene group may be substituted with an oxygen atom to form a chain-like or cyclic ether or two hydrogen atoms on a common carbon may be substituted with an oxygen atom to form a ketone. In case of p=0, for example, exemplary Z' groups are methylene, ethylene, trimethylene, tetramethylene, pentamethylene, 1,2-propanediyl, 1,3-butanediyl, 1-oxo-2-oxapropane-1,3-diyl, and 3-methyl-1-oxo-2-oxabutane-1,4-diyl. In case of p≠0, exemplary Z' groups are (p+2)-valent groups obtained by eliminating one or two hydrogen atoms from the above-exemplified groups. The letter k' is 0 or 1, and p is 0, 1 or 2.

The acid labile groups represented by $R^d$, $R^{d'}$ and $R^{O15}$ may be selected from a variety of such groups. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

(L1)

(L2)

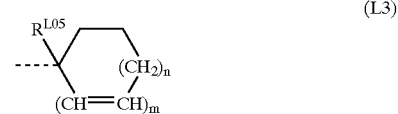

(L3)

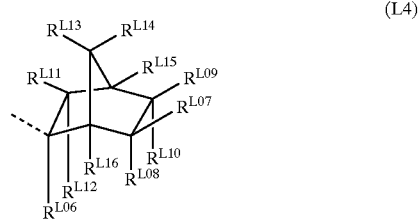

(L4)

In these formulae and throughout the specification, the broken line denotes a free valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, and n-octyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and straight, branched or cyclic alkyl groups in which some hydrogen atoms are replaced by hydroxyl, alkoxy, oxo, amino, alkylamino or the like. Illustrative examples are the substituted alkyl groups shown below.

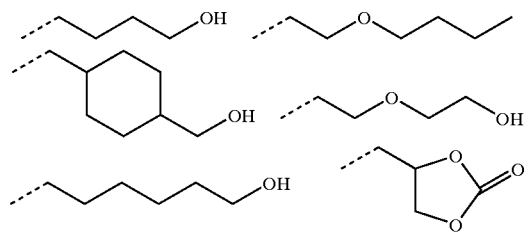

A pair of $R^{L01}$ and $R^{L02}$, $R^{L01}$ and $R^{L03}$, or $R^{L02}$ and $R^{L03}$ may bond together to form a ring. Each of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl) propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

$R^{L05}$ is a monovalent hydrocarbon group of 1 to 8 carbon atoms which may contain a hetero atom or a substituted or unsubstituted aryl group of 6 to 20 carbon atoms. Examples of the monovalent hydrocarbon group which may contain a hetero atom include straight, branched or cyclic alkyl groups such as methyl, ethyl, propyl, isopropyl, n-butyl, sec-butyl, tert-butyl, tert-amyl, n-pentyl, n-hexyl, cyclopentyl, and cyclohexyl, and substituted groups in which some hydrogen atoms on the foregoing groups are substituted with hydroxyl, alkoxy, carboxy, alkoxycarbonyl, oxo, amino, alkylamino, cyano, mercapto, alkylthio, sulfo or other groups. Exemplary aryl groups are phenyl, methylphenyl, naphthyl, anthryl, phenanthryl, and pyrenyl. Letter m is equal to 0 or 1, n is equal to 0, 1, 2 or 3, and 2m+n is equal to 2 or 3.

$R^{L06}$ is a monovalent hydrocarbon group of 1 to 8 carbon atoms which may contain a hetero atom or a substituted or unsubstituted aryl group of 6 to 20 carbon atoms. Examples of these groups are the same as exemplified for $R^{L05}$.

$R^{L07}$ to $R^{L16}$ independently represent hydrogen or monovalent hydrocarbon groups of 1 to 15 carbon atoms which may contain a hetero atom. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted ones of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$, taken together, form a ring (for example, a pair of $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$—$C_{15}$ hydrocarbon group which may contain a hetero atom, when they form a ring, examples of which are the ones exemplified above for the monovalent hydrocarbon groups, with one hydrogen atom being eliminated. Two of $R^{L07}$ to $R^{L16}$ which are attached to adjoining carbon atoms (for example, a pair of $R^{L07}$ and $R^{L09}$, $R^{L09}$ and $R^{L15}$, $R^{L13}$ and $R^{L15}$, or a similar pair) may bond together directly to form a double bond.

Of the acid labile groups of formula (L1), the straight and branched ones are exemplified by the following groups.

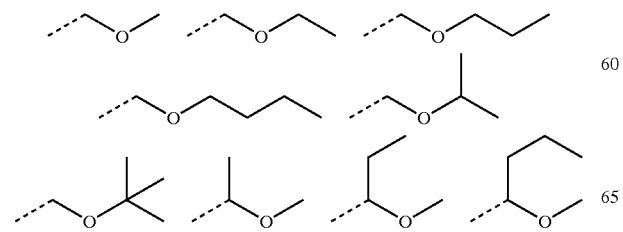

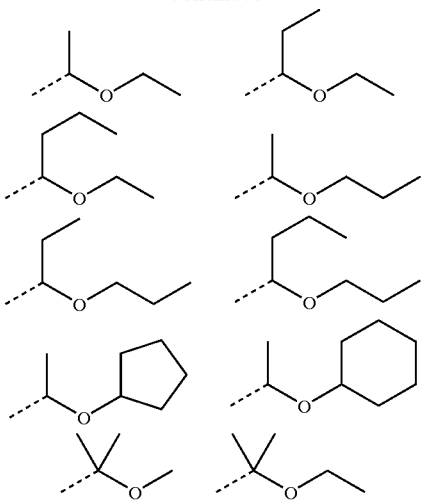

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl) cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

The acid labile groups of formula (L4) are exemplified by the following groups.

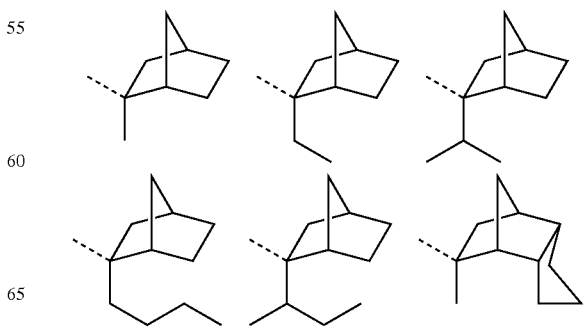

-continued

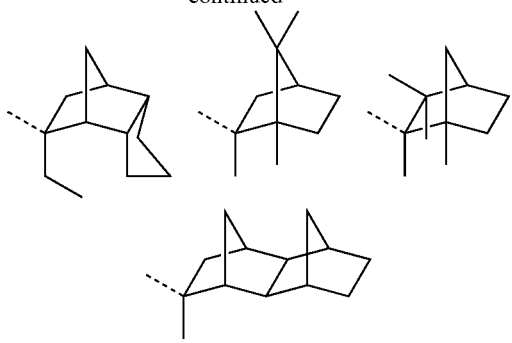

Examples of the tertiary alkyl groups of 4 to 20 carbon atoms, trialkylsilyl groups in which each alkyl moiety has 1 to 6 carbon atoms, and oxoalkyl groups of 4 to 20 carbon atoms are as exemplified for $R^{L04}$.

$R^{001}$ is hydrogen, methyl or $CH_2CO_2R^{003}$. $R^{002}$ is hydrogen, methyl or $CO_2R^{003}$. $R^{003}$ is a straight, branched or cyclic alkyl group of 1 to 15 carbon atoms, for example, methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, and butyladamantyl.

$R^{004}$ is hydrogen or a monovalent hydrocarbon group of 1 to 15 carbon atoms having a carboxyl or hydroxyl group, for example, hydrogen, carboxyethyl, carboxybutyl, carboxycyclopentyl, carboxycyclohexyl, carboxynorbornyl, carboxyadamantyl, hydroxyethyl, hydroxybutyl, hydroxycyclopentyl, hydroxycyclohexyl, hydroxynorbornyl, and hydroxyadamantyl.

At least one of $R^{005}$ to $R^{008}$ represents a monovalent hydrocarbon group of 1 to 15 carbon atoms having a carboxyl or hydroxyl group while the remaining R's independently represent hydrogen or a straight, branched or cyclic alkyl group of 1 to 15 carbon atoms. Examples of the carboxyl or hydroxyl-bearing monovalent hydrocarbon group of 1 to 15 carbon atoms include carboxy, carboxymethyl, carboxyethyl, carboxybutyl, hydroxymethyl, hydroxyethyl, hydroxybutyl, 2-carboxyethoxycarbonyl, 4-carboxybutoxycarbonyl, 2-hydroxyethoxycarbonyl, 4-hydroxybutoxycarbonyl, carboxycyclopentyloxycarbonyl, carboxycyclohexyloxycarbonyl, carboxynorbornyloxycarbonyl, carboxyadamantyloxycarbonyl, hydroxycyclopentyloxycarbonyl, hydroxycyclohexyloxycarbonyl, hydroxynorbornyloxycarbonyl, and hydroxyadamantyloxycarbonyl. Examples of the straight, branched or cyclic alkyl group of 1 to 15 carbon atoms are the same as exemplified for $R^b$.

Alternatively, $R^{005}$ to $R^{008}$, taken together, may form a ring, and in that event, at least one of $R^{005}$ to $R^{008}$ is a divalent hydrocarbon group of 1 to 15 carbon atoms having a carboxyl or hydroxyl group, while the remaining R's are independently single bonds or straight, branched or cyclic alkylene groups of 1 to 15 carbon atoms. Examples of the carboxyl or hydroxyl-bearing divalent hydrocarbon group of 1 to 15 carbon atoms include the groups exemplified as the carboxyl or hydroxyl-bearing monovalent hydrocarbon group, with one hydrogen atom eliminated therefrom. Examples of the straight, branched or cyclic alkylene groups of 1 to 15 carbon atoms include the groups exemplified for $R^b$, with one hydrogen atom eliminated therefrom.

$R^{009}$ is a monovalent hydrocarbon group of 2 to 15 carbon atoms containing at least one partial structure selected from among ether, aldehyde, ketone, ester, carbonate, acid anhydride, amide and imide, for example, methoxymethyl, methoxyethoxymethyl, 2-oxooxolan-3-yl, 2-oxooxolan-4-yl, 4,4-dimethyl-2-oxooxolan-3-yl, 4-methyl-2-oxooxan-4-yl, 2-oxo-1,3-dioxolan-4-ylmethyl, and 5-methyl-2-oxooxolan-5-yl.

At least one of $R^{010}$ to $R^{013}$ is a monovalent hydrocarbon group of 2 to 15 carbon atoms containing at least one partial structure selected from among ether, aldehyde, ketone, ester, carbonate, acid anhydride, amide and imide, while the remaining R's are independently hydrogen or straight, branched or cyclic alkyl groups of 1 to 15 carbon atoms. Examples of the monovalent hydrocarbon group of 2 to 15 carbon atoms containing at least one partial structure selected from among ether, aldehyde, ketone, ester, carbonate, acid anhydride, amide and imide include methoxymethyl, methoxymethoxymethyl, formyl, methylcarbonyl, formyloxy, acetoxy, pivaloyloxy, formyloxymethyl, acetoxymethyl, pivaloyloxymethyl, methoxycarbonyl, 2-oxooxolan-3-yloxycarbonyl, 4,4-dimethyl-2-oxooxolan-3-yloxycarbonyl, 4-methyl-2-oxooxan-4-yloxycarbonyl, 2-oxo-1,3-dioxolan-4-ylmethyloxycarbonyl, and 5-methyl-2-oxooxolan-5-yloxycarbonyl. Examples of the straight, branched or cyclic alkyl groups of 1 to 15 carbon atoms are the same as exemplified for $R^{003}$.

$R^{010}$ to $R^{013}$, taken together, may form a ring, and in that event, at least one of $R^{010}$ to $R^{013}$ is a divalent hydrocarbon group of 1 to 15 carbon atoms containing at least one partial structure selected from among ether, aldehyde, ketone, ester, carbonate, acid anhydride, amide and imide, while the remaining R's are independently single bonds or straight, branched or cyclic alkylene groups of 1 to 15 carbon atoms. Examples of the divalent hydrocarbon group of 1 to 15 carbon atoms containing at least one partial structure selected from among ether, aldehyde, ketone, ester, carbonate, acid anhydride, amide and imide include 2-oxapropane-1,3-diyl, 1,1-dimethyl-2-oxapropane-1,3-diyl, 1-oxo-2-oxapropane-1,3-diyl, 1,3-dioxo-2-oxapropane-1,3-diyl, 1-oxo-2-oxabutane-1,4-diyl, and 1,3-dioxo-2-oxabutane-1,4-diyl, as well as the groups exemplified as the monovalent hydrocarbon group of 1 to 15 carbon atoms containing at least one partial structure selected from among ether, aldehyde, ketone, ester, carbonate, acid anhydride, amide and imide, with one hydrogen atom eliminated therefrom. Examples of the straight, branched or cyclic alkylene groups of 1 to 15 carbon atoms include the groups exemplified for $R^{003}$, with one hydrogen atom eliminated therefrom.

$R^{014}$ is a polycyclic hydrocarbon group having 7 to 15 carbon atoms or an alkyl group containing a polycyclic hydrocarbon group, for example, norbornyl, bicyclo[3.3.1]nonyl, tricyclo[5.2.1.0$^{2,6}$]decyl, adamantyl, ethyladamantyl, butyladamantyl, norbornylmethyl, and adamantylmethyl.

$R^{015}$ is an acid labile group, examples of which are the same as described above for $R^d$ and $R^{d'}$. X is $CH_2$ or an oxygen atom. Letter k is equal to 0 or 1.

In addition to the recurring units described above, the polymer of the invention may include recurring units obtained from an additional monomer having a carbon-to-carbon double bond. Examples of the additional monomer include substituted acrylic acid esters such as methyl methacrylate, methyl crotonate, dimethyl maleate, and dimethyl itaconate, unsaturated carboxylic acids such as maleic acid, fumaric acid and itaconic acid, substituted or unsubstituted norbornenes such as norbornene and methyl norbornene-5-carboxylate, and unsaturated acid anhydrides such as itaconic anhydride.

The polymers of the invention should preferably have a weight average molecular weight of about 1,000 to 500,000, preferably about 3,000 to 100,000, as measured by gel permeation chromatography (GPC) using a polystyrene standard. Outside the range, the etching resistance may become extremely low and the resolution may become low because a substantial difference In rate of dissolution before and after exposure is lost.

In the polymers of the invention, the preferred proportion of recurring units based on the respective monomers is in the following range (in mol %), though not limited thereto.

(I) When the polymer is comprised of recurring units of formula (1a) and recurring units of formula (M1), it contains
(i) 1 to 90%, preferably 5 to 80%, and more preferably 10 to 70% of recurring units of formula (1a),
(ii) 1 to 90%, preferably 5 to 80%, and more preferably 10 to 70% of recurring units of formula (M1),
(iii) 0 to 50%, preferably 0 to 40%, and more preferably 0 to 30% of recurring units of formulae (M9) to (M12), and
(iv) 0 to 50%, preferably 0 to 40%, and more preferably 0 to 30% of recurring units based on another monomer.

(II) When the polymer is comprised of recurring units of formula (1a), recurring units of formula (M1) and recurring units of formula (M3), it contains
(i) 1 to 49%, preferably 3 to 45%, and more preferably 5 to 40% of recurring units of formula (1a),
(ii) 1 to 49%, preferably 3 to 45%, and more preferably 5 to 40% of recurring units of formula (M1),
(iii) 50 mol % of recurring units of formula (M3),
(iv) 0 to 25%, preferably 0 to 20%, and more preferably 0 to 15% of recurring units of formula (M9) to (M12), and
(v) 0 to 25%, preferably 0 to 20%, and more preferably 0 to 15% of recurring units based on another monomer.

(III) When the polymer is comprised of recurring units of formula (1a), recurring units of formula (M4) alone or in combination with recurring units of formula (M1), and recurring units of formula (M3), it contains
(i) 1 to 49%, preferably 3 to 45%, and more preferably 5 to 40% of recurring units of formula (1a),
(ii) 0 to 40%, preferably 0 to 35%, and more preferably 0 to 30% of recurring units of formula (M1),
(iii) 1 to 80%, preferably 1 to 70%, and more preferably 1 to 50% of recurring units of formula (M4),
(iv) 1 to 49%, preferably 5 to 45%, and more preferably 10 to 40% of recurring units of formula (M3),
(v) 0 to 25%, preferably 0 to 20%, and more preferably 0 to 15% of recurring units of formula (M5) to (M12), and
(vi) 0 to 25%, preferably 0 to 20%, and more preferably 0 to 15% of recurring units based on another monomer.

(IV) When the polymer is comprised of recurring units of formula (1a) and recurring units of formula (M4), it contains
(i) 1 to 90%, preferably 5 to 80%, and more preferably 10 to 70% of recurring units of formula (1a),
(ii) 1 to 90%, preferably 5 to 80%, and more preferably 10 to 70% of recurring units of formula (M4),
(iii) 0 to 50%, preferably 0 to 40%, and more preferably 0 to 30% of recurring units of formula (M5) to (M12), and
(iv) 0 to 50%, preferably 0 to 40%, and more preferably 0 to 30% of recurring units based on another monomer.

(V) When the polymer is comprised of recurring units of formula (2a) and recurring units of formula (M2), it contains
(i) 1 to 90%, preferably 5 to 80%, and more preferably 10 to 70% of recurring units of formula (2a),
(ii) 1 to 90%, preferably 5 to 80%, and more preferably 10 to 70% of recurring units of formula (M2),
(iii) 0 to 50%, preferably 0 to 40%, and more preferably 0 to 30% of recurring units of formula (M13) to (M16), and
(iv) 0 to 50%, preferably 0 to 40%, and more preferably 0 to 30% of recurring units based on another monomer.

The polymer of the invention can be prepared through copolymerization reaction using a compound of formula (1) as a first monomer and at least one compound having a polymerizable double bond as second and subsequent monomers.

A variety of copolymerization reaction methods may be used for the preparation of the polymer according to the invention. The preferred polymerization reaction is radical polymerization, anionic polymerization or coordination polymerization.

For radical polymerization, preferred reaction conditions include (a) a solvent selected from among hydrocarbons such as benzene, ethers such as tetrahydrofuran, alcohols such as ethanol, and ketones such as methyl isobutyl ketone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about ½ hour to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about ½ hour to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about ½ hour to about 48 hours. Reaction conditions outside the described range may be employed if desired.

Resist Composition

Since the polymer of the invention is useful as the base resin of a resist composition, the third aspect of the invention provides a resist composition, especially a chemically amplified positive resist composition, comprising the polymer. Typically, the resist composition contains the polymer, a photoacid generator, and an organic solvent, and other optional components.

Photoacid Generator

The photoacid generator is a compound capable of generating an acid upon exposure to high energy radiation or electron beams and includes the following:
(i) onium salts of the formula (P1a-1), (P1a-2) or (P1b),
(ii) diazomethane derivatives of the formula (P2),
(iii) glyoxime derivatives of the formula (P3),
(iv) bissulfone derivatives of the formula (P4),
(v) sulfonic acid esters of N-hydroxyimide compounds of the formula (P5),
(vi) β-ketosulfonic acid derivatives,
(vii) disulfone derivatives, (viii) nitrobenzylsulfonate derivatives, and
(ix) sulfonate derivatives.

These photoacid generators are described in detail.

(i) Onium salts of formula (P1a-1), (P1a-2) or (P1b):

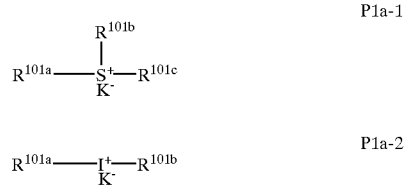

Herein, $R^{101a}$, $R^{101b}$, and $R^{101c}$ independently represent straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. $K^-$ is a non-nucleophilic counter ion.

$R^{101a}$, $R^{101b}$, and $R^{101c}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl. Examples of the non-nucleophilic counter ion represented by $K^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

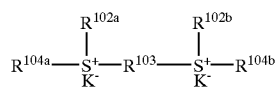

Herein, $R^{102a}$ and $R^{102b}$ independently represent straight, branched or cyclic alkyl groups of 1 to 8 carbon atoms. $R^{103}$ represents a straight, branched or cyclic alkylene groups of 1 to 10 carbon atoms. $R^{104a}$ and $R^{104b}$ independently represent 2-oxoalkyl groups of 3 to 7 carbon atoms. $K^-$ is a non-nucleophilic counter ion.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl. Illustrative examples of the counter ion represented by $K^-$ are the same as exemplified for formulae (P1a-1) and (P1a-2).

(ii) Diazomethane derivatives of formula (P2)

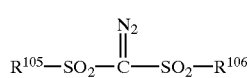

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime derivatives of formula (P3)

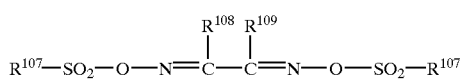

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ each are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone derivatives of formula (P4)

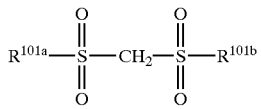

Herein, $R^{101a}$ and $R^{101b}$ are as defined above.

(v) Sulfonic acid esters of N-hydroxyimide compounds of formula (P5)

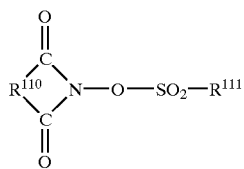

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups. $R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), hetero-aromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, ethylene, trimethylene, tetramethylene, phenylethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; the alkoxy groups of 1 to 4 carbon atoms include methoxy, ethoxy, propoxy, isopropoxy, n-butoxy, isobutoxy, and tert-butoxy; the phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl; the hetero-aromatic groups of 3 to 5 carbon atoms include pyridyl and furyl.

Illustrative examples of the photoacid generator include: onium salts such as diphenyliodonium trifluoromethanesulfonate, (p-tert-butoxyphenyl) phenyliodonium trifluoromethanesulfonate, diphenyliodonium p-toluenesulfonate, (p-tert-butoxyphenyl) phenyliodonium p-toluenesulfonate, triphenylsulfonium trifluoromethanesulfonate, (p-tert-butoxyphenyl) diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl) diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl) sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylenebis[methyl(2-oxocyclopentyl)sulfonium trifluoromethanesulfonate], and 1,2'-naphthylcarbonylmethyltetrahydrothiophenium triflate;

diazomethane derivatives such as bis(benzenesulfonyl) diazomethane, bis(p-toluenesulfonyl)diazomethane, bis (xylenesulfonyl)diazomethane, bis(cyclohexylsulfonyl) diazomethane, bis(cyclopentylsulfonyl)diazomethane, bis (n-butylsulfonyl)diazomethane, bis(isobutylsulfonyl) diazomethane, bis(sec-butylsulfonyl)diazomethane, bis(n-propylsulfonyl)diazomethane, bis(isopropylsulfonyl) diazomethane, bis(tert-butylsulfonyl)diazomethane, bis(n-amylsulfonyl)diazomethane, bis(isoamylsulfonyl) diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, and 1-tert-amylsulfonyl-1-(tert-butylsulfonyl)diazomethane;

glyoxime derivatives such as bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(p-toluenesulfonyl)-2-methyl-3,4-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(n-butanesulfonyl)-2,3-pentanedioneglyoxime, bis-O-(n-butanesulfonyl)-2-methyl-3,4-pentanedioneglyoxime, bis-O-(methanesulfonyl)-α-dimethylglyoxime, bis-O-(trifluoromethanesulfonyl)-α-dimethylglyoxime, bis-O-(1,1,1-trifluoroethanesulfonyl)-α-dimethylglyoxime, bis-O-(tert-butanesulfonyl)-α-dimethylglyoxime, bis-O-(perfluorooctanesulfonyl)-α-dimethylglyoxime, bis-O-(cyclohexanesulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-tert-butylbenzenesulfonyl)-α-dimethylglyoxime, bis-O-(xylenesulfonyl)-α-dimethylglyoxime, and bis-O-(camphorsulfonyl)-α-dimethylglyoxime;

bissulfone derivatives such as bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane;

β-ketosulfone derivatives such as 2-cyclohexyl-carbonyl2-(p-toluenesulfonyl)propane and 2-isopropylcarbonyl-2-(p-toluenesulfonyl)propane;

disulfone derivatives such as diphenyl disulfone and dicyclohexyl disulfone;

nitrobenzyl sulfonate derivatives such as 2,6-dinitrobenzyl p-toluenesulfonate and 2,4-dinitrobenzyl p-toluenesulfonate;

sulfonic acid ester derivatives such as 1,2,3-tris(methanesulfonyloxy)benzene, 1,2,3-tris(trifluoromethanesulfonyloxy)benzene, and 1,2,3-tris(p-toluenesulfonyloxy)benzene; and sulfonic acid esters of N-hydroxyimides such as N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethylbenzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethanesulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N-hydroxyphthalimide trifluoromethanesulfonate, N-hydroxyphthalimide p-toluenesulfonate, N-hydroxynaphthalimide methanesulfonate, N-hydroxynaphthalimide benzenesulfonate, N-hydroxy-5-norbornene-2,3-dicarboxyimide methanesulfonate, N-hydroxy-5-norbornene-2,3-dicarboxyimide trifluoromethanesulfonate, and N-hydroxy-5-norbornene-2,3-dicarboxyimide p-toluenesulfonate.

Preferred among these photoacid generators are onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocylohexyl)sulfonium trifluoromethanesulfonate, and 1,2'-naphthylcarbonylmethyltetrahydrothiophenium triflate; diazomethane derivatives such as bis(benzenesulfonyl) diazomethane, bis(p-toluenesulfonyl)diazomethane, bis (cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis (tert-butylsulfonyl)diazomethane; glyoxime derivatives such as bis-O-(p-toluenesulfonyl)-α-dimethylglyoxime and bis-O-(n-butanesulfonyl)-α-dimethylglyoxime; bissulfone derivatives such as bisnaphthylsulfonylmethane; and sulfonic acid esters of N-hydroxyimide compounds such as N-hydroxysuccinimide methanesulfonate, N-hydroxysuccinimide trifluoromethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide p-toluenesulfonate, N-hydroxynaphthalimide methanesulfonate, and N-hydroxynaphthalimide benzenesulfonate.

These photoacid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The photoacid generator is added in an amount of 0.1 to 15 parts, and especially 0.5 to 8 parts by weight, per 100 parts by weight of the base resin (all parts are by weight, hereinafter). Less than 0.1 part of the photoacid generator would provide a poor sensitivity whereas more than 15 parts of the photoacid generator would adversely affect transparency and resolution.

Organic Solvent

The organic solvent used herein may be any organic solvent in which the base resin, photoacid generator, and other components are soluble. Illustrative, non-limiting, examples of the organic solvent include ketones such as cyclohexanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. These solvents may be used alone or in combinations of two or more thereof. Of the above organic solvents, it is recommended to use diethylene glycol dimethyl ether and 1-ethoxy-2-propanol because the photoacid generator is most soluble therein, propylene glycol monomethyl ether acetate because it is a safe solvent, or a mixture thereof.

An appropriate amount of the organic solvent used is about 200 to 1,000 parts, especially about 400 to 800 parts by weight per 100 parts by weight of the base resin.

Other Polymer

To the resist composition of the invention, another polymer other than the inventive polymer may also be added. The other polymers that can be added to the resist composition are, for example, those polymers comprising units of the following formula (R1) and/or (R2) and having a weight average molecular weight of about 1,000 to about 500,000, especially about 5,000 to about 100,000 although the other polymers are not limited thereto.

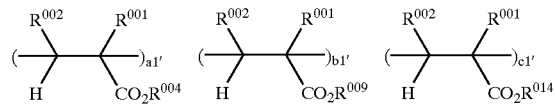

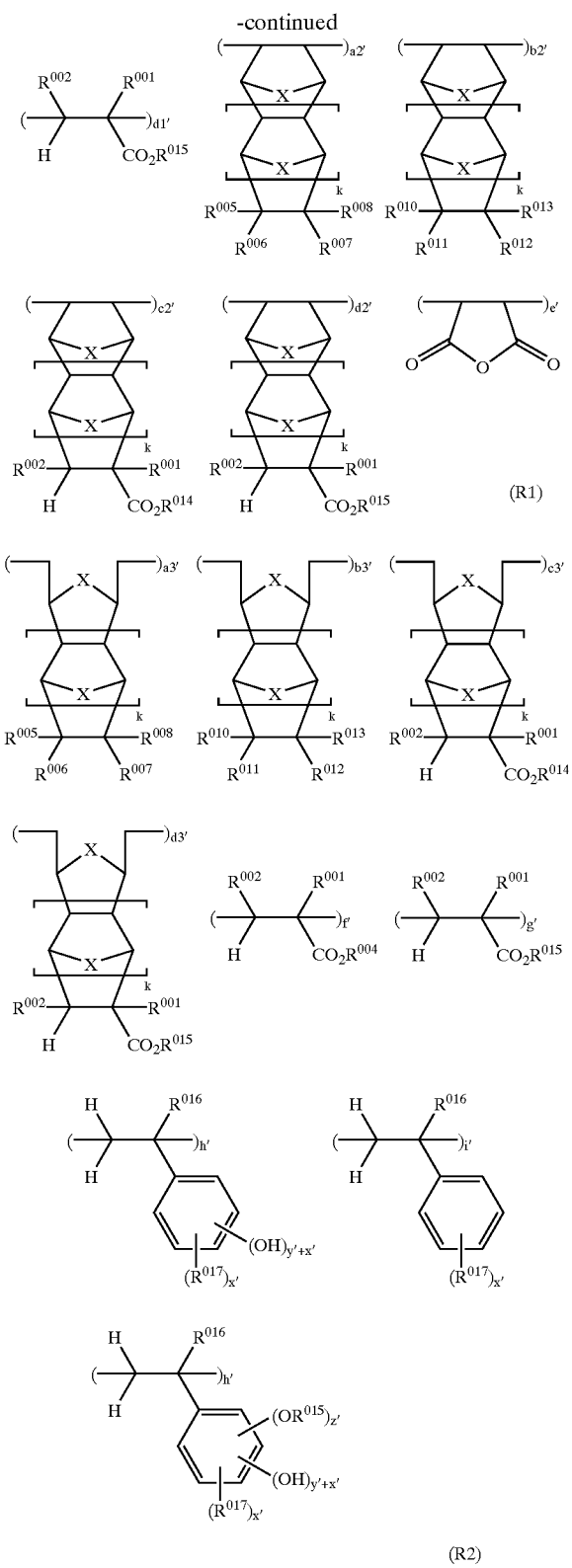

group of 1 to 15 carbon atoms having a carboxyl or hydroxyl group while the remaining R's independently represent hydrogen or a straight, branched or cyclic alkyl group of 1 to 15 carbon atoms. Alternatively, $R^{005}$ to $R^{008}$, taken together, may form a ring, and in that event, at least one of $R^{005}$ to $R^{008}$ is a divalent hydrocarbon group of 1 to 15 carbon atoms having a carboxyl or hydroxyl group, while the remaining R's are independently single bonds or straight, branched or cyclic alkylene groups of 1 to 15 carbon atoms. $R^{009}$ is a monovalent hydrocarbon group of 2 to 15 carbon atoms containing at least one partial structure selected from among ether, aldehyde, ketone, ester, carbonate, acid anhydride, amide and imide. At least one of $R^{010}$ to $R^{013}$ is a monovalent hydrocarbon group of 2 to 15 carbon atoms containing at least one partial structure selected from among ether, aldehyde, ketone, ester, carbonate, acid anhydride, amide and imide, while the remaining R's are independently hydrogen or straight, branched or cyclic alkyl groups of 1 to 15 carbon atoms. $R^{010}$ to $R^{013}$, taken together, may form a ring, and in that event, at least one of $R^{010}$ to $R^{013}$ is a divalent hydrocarbon group of 1 to 15 carbon atoms containing at least one partial structure selected from among ether, aldehyde, ketone, ester, carbonate, acid anhydride, amide and imide, while the remaining R's are independently single bonds or straight, branched or cyclic alkylene groups of 1 to 15 carbon atoms. $R^{014}$ is a polycyclic hydrocarbon group having 7 to 15 carbon atoms or an alkyl group containing a polycyclic hydrocarbon group. $R^{015}$ is an acid labile group. $R^{016}$ is hydrogen or methyl. $R^{017}$ is a straight, branched or cyclic alkyl group of 1 to 8 carbon atoms. X is $CH_2$ or an oxygen atom. Letter k' is equal to 0 or 1; a1', a2', a3', b1', b2', b3', c1', c2', c3', d1', d2', d3', and e' are numbers from 0 to less than 1, satisfying a1'+a2'+a3'+b1'+b2'+b3'+c1'+c2'+c3'+d1'+d2'+d3'+e'=1; f', g', h', i', and j' are numbers from 0 to less than 1, satisfying f'+g'+h'+i'+j'=1; x', y' and z' each are an integer of 0 to 3, satisfying $1 \leq x'+y'+z' \leq 5$ and $1 \leq y'+z' \leq 3$. Exemplary groups of these R's are as exemplified above.

The inventive polymer and the other polymer are preferably blended in a weight ratio from 100:0 to 10:90, more preferably from 100:0 to 20:80. If the blend ratio of the inventive polymer is below this range, the resist composition would become poor in some of the desired properties. The properties of the resist composition can be adjusted by properly changing the blend ratio of the inventive polymer.

The other polymer is not limited to one type and a mixture of two or more other polymers may be added. The use of plural polymers allows for easy adjustment of resist properties.

Dissolution Regulator

To the resist composition, a dissolution regulator may be added. The dissolution regulator is a compound having on the molecule at least two phenolic hydroxyl groups, in which an average of from 0 to 100 mol % of all the hydrogen atoms on the phenolic hydroxyl groups are replaced with acid labile groups or a compound having on the molecule at least one carboxyl group, in which an average of 50 to 100 mol % of all the hydrogen atoms on the carboxyl groups are replaced with acid labile groups, both the compounds having an average molecular weight within a range of 100 to 1,000, and preferably 150 to 800.

The degree of substitution of the hydrogen atoms on the phenolic hydroxyl groups with acid labile groups is on average at least 0 mol %, and preferably at least 30 mol %, of all the phenolic hydroxyl groups. The upper limit is 100 mol %, and preferably 80 mol %. The degree of substitution of the hydrogen atoms on the carboxyl groups with acid Herein, $R^{001}$ is hydrogen, methyl or $CH_2CO_2R^{003}$. $R^{002}$ is hydrogen, methyl or $CO_2R^{003}$. $R^{003}$ is a straight, branched or cyclic alkyl group of 1 to 15 carbon atoms. $R^{004}$ is hydrogen or a monovalent hydrocarbon group of 1 to 15 carbon atoms having a carboxyl or hydroxyl group. At least one of $R^{005}$ to $R^{008}$ represents a monovalent hydrocarbon labile groups is on average at least 50 mol %, and preferably at least 70 mol %, of all the carboxyl groups, with the upper limit being 100 mol %.

Preferable examples of such compounds having two or more phenolic hydroxyl groups or compounds having at least one carboxyl group include those of formulas (D1) to (D14) below.

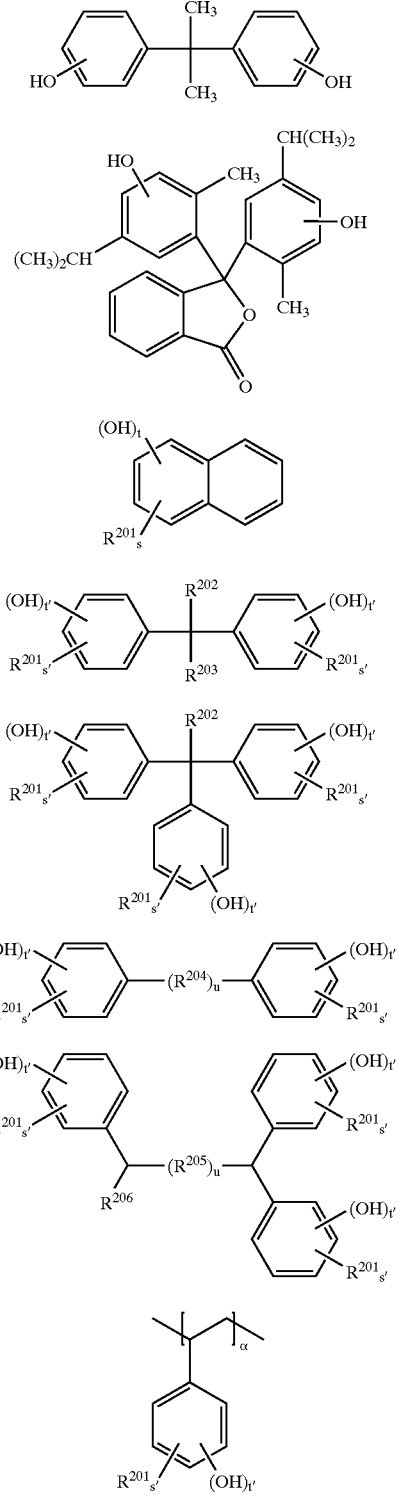

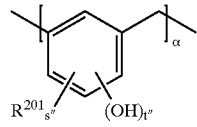

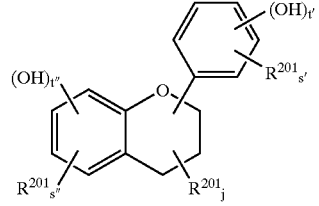

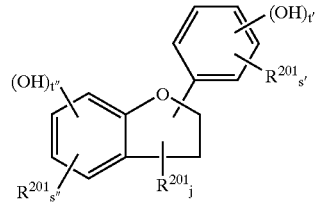

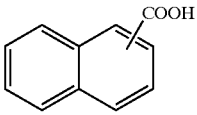

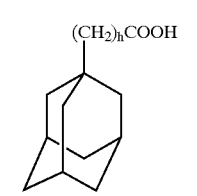

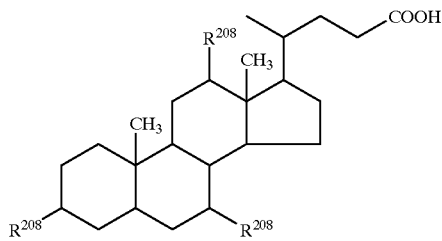

In these formulas, $R^{201}$ and $R^{202}$ are each hydrogen or a straight or branched alkyl or alkenyl of 1 to 8 carbon atoms; $R^{203}$ is hydrogen, a straight or branched alkyl or alkenyl of 1 to 8 carbon atoms, or —$(R^{207})_h$—COOH; $R^{204}$ is —$(CH_2)_i$— (where i=2 to 10), an arylene of 6 to 10 carbon atoms, carbonyl, sulfonyl, an oxygen atom, or a sulfur atom; $R^{205}$ is an alkylene of 1 to 10 carbon atoms, an arylene of 6 to 10 carbon atoms, carbonyl, sulfonyl, an oxygen atom, or a sulfur atom; $R^{206}$ is hydrogen, a straight or branched alkyl or alkenyl of 1 to 8 carbon atoms, or a hydroxyl-substituted phenyl or naphthyl; $R^{207}$ is a straight or branched alkylene of 1 to 10 carbon atoms; $R^{208}$ is hydrogen or hydroxyl; the letter j is an integer from 0 to 5; u and h are each 0 or 1; s, t, s', t', s", and t" are each numbers which satisfy s+t=8, s'+t'=5, and s"+t"=4, and are such that each phenyl skeleton has at least one hydroxyl group; and α is a number such that the compounds of formula (D8) or (D9) have a molecular weight of from 100 to 1,000.

In the above formulas, suitable examples of $R^{201}$ and $R^{202}$ include hydrogen, methyl, ethyl, butyl, propyl, ethynyl, and cyclohexyl; suitable examples of $R^{203}$ include the same groups as for $R^{201}$ and $R^{202}$, as well as —COOH and —CH$_2$COOH; suitable examples of $R^{204}$ include ethylene, phenylene, carbonyl, sulfonyl, oxygen, and sulfur; suitable examples of $R^{205}$ include methylene as well as the same groups as for $R^{204}$; and suitable examples of $R^{206}$ include hydrogen, methyl, ethyl, butyl, propyl, ethynyl, cyclohexyl, and hydroxyl-substituted phenyl or naphthyl.

Exemplary acid labile groups on the dissolution regulator include groups of the following general formulae (L1) to (L4), tertiary alkyl groups of 4 to 20 carbon atoms, trialkylsilyl groups in which each of the alkyls has 1 to 6 carbon atoms, and oxoalkyl groups of 4 to 20 carbon atoms.

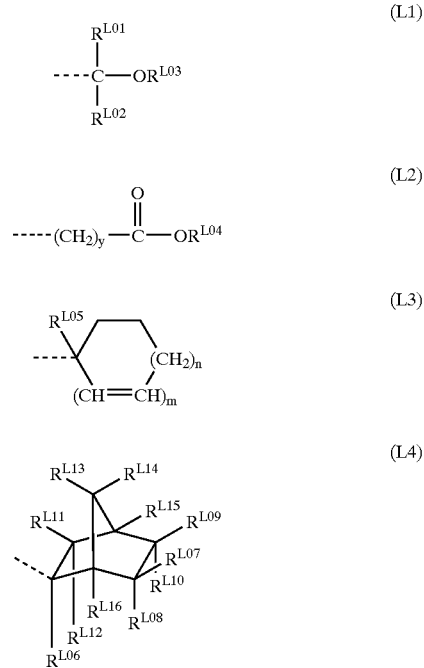

In these formulas, $R^{L01}$ and $R^{L02}$ are each hydrogen or a straight, branched or cyclic alkyl having 1 to 18 carbon atoms; and $R^{L03}$ is a monovalent hydrocarbon group of 1 to 18 carbon atoms which may contain a heteroatom (e.g., oxygen). A pair of $R^{L01}$ and $R^{L02}$, a pair of $R^{L01}$ and $R^{L03}$, or a pair of $R^{L02}$ and $R^{L03}$ may together form a ring, with the proviso that $R^{L01}$, $R^{L02}$, and $R^{L03}$ are each a straight or branched alkylene of 1 to 18 carbon atoms when they form a ring. $R^{L04}$ is a tertiary alkyl group of 4 to 20 carbon atoms, a trialkysilyl group in which each of the alkyls has 1 to 6 carbon atoms, an oxoalkyl group of 4 to 20 carbon atoms, or a group of the formula (L1). $R^{L05}$ is a monovalent hydrocarbon group of 1 to 8 carbon atoms which may contain a hetero atom or a substituted or unsubstituted aryl group of 6 to 20 carbon atoms. $R^{L06}$ is a monovalent hydrocarbon group of 1 to 8 carbon atoms which may contain a hetero atom or a substituted or unsubstituted aryl group of 6 to 20 carbon atoms. $R^{L07}$ to $R^{L16}$ independently represent hydrogen or monovalent hydrocarbon groups of 1 to 15 carbon atoms which may contain a hetero atom. Alternatively, $R^{L07}$ to $R^{L16}$, taken together, may form a ring. Each of $R^{L07}$ to $R^{L16}$ represents a divalent $C_1$—$C_{15}$ hydrocarbon group which may contain a hetero atom, when they form a ring. Two of $R^{L07}$ to $R^{L16}$ which are attached to adjoining carbon atoms may bond together directly to form a double bond. Letter y is an integer of 0 to 6. Letter m is equal to 0 or 1, n is equal to 0, 1, 2 or 3, and 2m+n is equal to 2 or 3. Illustrative examples of these groups are as previously exemplified.

The dissolution regulator may be formulated in an amount of 0 to 50 parts, preferably 0 to 40 parts, and more preferably 0 to 30 parts, per 100 parts of the base resin, and may be used singly or as a mixture of two or more thereof. The use of more than 50 parts would lead to slimming of the patterned film, and thus a decline in resolution.

The dissolution regulator can be synthesized by introducing acid labile groups into a compound having phenolic hydroxyl or carboxyl groups in accordance with an organic chemical formulation.

Basic Compound

In the resist composition of the invention, a basic compound may be blended. A suitable basic compound used herein is a compound capable of suppressing the rate of diffusion when the acid generated by the photoacid generator diffuses within the resist film. The inclusion of this type of basic compound holds down the rate of acid diffusion within the resist film, resulting in better resolution. In addition, it suppresses changes in sensitivity following exposure, thus reducing substrate and environment dependence, as well as improving the exposure latitude and the pattern profile.

Examples of basic compounds include primary, secondary, and tertiary aliphatic amines, mixed amines, aromatic amines, heterocyclic amines, carboxyl group-bearing nitrogenous compounds, sulfonyl group-bearing nitrogenous compounds, hydroxyl group-bearing nitrogenous compounds, hydroxyphenyl group-bearing nitrogenous compounds, alcoholic nitrogenous compounds, amide derivatives, and imide derivatives.

Examples of suitable primary aliphatic amines include ammonia, methylamine, ethylamine, n-propylamine, isopropylamine, n-butylamine, iso-butylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, di-iso-propylamine, di-n-butylamine, di-iso-butylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, tri-iso-propylamine, tri-n-butylamine, tri-iso-butylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-bearing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable sulfonyl group-bearing nitrogenous compounds include 3-pyridinesulfonic acid and pyridinium p-toluenesulfonate. Examples of suitable hydroxyl group-bearing nitrogenous compounds, hydroxyphenyl group-bearing nitrogenous compounds, and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, basic compounds of the following general formula (B1) may also be included alone or in admixture.

$$N(X^1)_{n1}(Y^1)_{3-n1} \qquad \text{B1}$$

In the formula, n1 is equal to 1, 2 or 3; $Y^1$ is independently hydrogen or a straight, branched or cyclic alkyl group of 1 to 20 carbon atoms which may contain a hydroxyl group or ether; and $X^1$ is independently selected from groups of the following general formulas (X1) to (X3), and two or three $X^1$'s may bond together to form a ring.

 X1

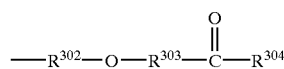 X2

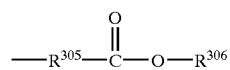 X3

In the formulas, $R^{300}$, $R^{302}$ and $R^{305}$ are independently straight or branched alkylene groups of 1 to 4 carbon atoms; $R^{301}$, $R^{304}$ and $R^{306}$ are independently hydrogen, straight, branched or cyclic alkyl groups of 1 to 20 carbon atoms, which may contain at least one hydroxyl group, ether, ester or lactone ring; and $R^{303}$ is a single bond or a straight or branched alkylene group of 1 to 4 carbon atoms.

Illustrative examples of the basic compounds of formula (B1) include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]ethylamine, N,N-bis(2-acetoxyethyl)-2-[(methoxycarbonyl)methoxycarbonyl]ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)ethylamine, N,N-bis(2-acetoxyethyl)-2-

(tetrahydrofurfuryloxycarbonyl)ethylamine, N,N-bis(2-hydroxyethyl)-2-[(2-oxotetrahydrofuran-3-yl)oxycarbonyl] ethylamine, N,N-bis(2-acetoxyethyl)-2-[(2-oxotetrahydrofuran-3-yl)oxycarbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl) ethylamine, N,N-bis(2-methoxyethyl)-2-(methoxycarbonyl) ethylamine, N-(2-hydroxyethyl)-bis[2-(methoxycarbonyl) ethyl]amine, N-(2-acetoxyethyl)-bis[2-(methoxycarbonyl) ethyl]amine, N-(2-hydroxyethyl)-bis[2-(ethoxycarbonyl) ethyl]amine, N-(2-acetoxyethyl)-bis[2-(ethoxycarbonyl) ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis [2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris (methoxycarbonylmethyl)amine, tris (ethoxycarbonylmethyl)amine, N-butyl-bis (methoxycarbonylmethyl)amine, N-hexyl-bis (methoxycarbonylmethyl)amine, and β-(diethylamino)-δ-valerolactone.

Also useful are one or more of cyclic structure-bearing basic compounds having the following general formula (B2).

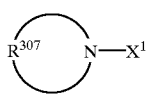

B2

Herein $X^1$ is as defined above, and $R^{307}$ is a straight or branched alkylene group of 2 to 20 carbon atoms which may contain one or more carbonyl groups, ether structures, ester structures or sulfide structures.

Illustrative examples of the cyclic structure-bearing basic compounds having formula (B2) include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino) propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl) propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl) methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

Also, one or more of cyano-bearing basic compounds having the following general formulae (B3) to (B6) may be blended.

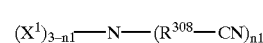

B3

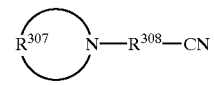

B4

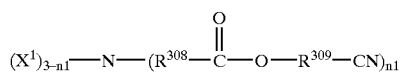

B5

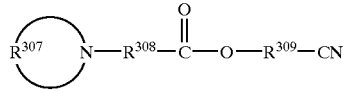

B6

Herein, $X^1$, $R^{307}$ and n1 are as defined above, and $R^{308}$ and $R^{309}$ each are independently a straight or branched alkylene group of 1 to 4 carbon atoms.

Illustrative examples of the cyano-bearing basic compounds having formulae (B3) to (B6) include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl) aminoacetonitrile, N,N-bis(2-acetoxyethyl) aminoacetonitrile, N,N-bis(2-formyloxyethyl) aminoacetonitrile, N,N-bis(2-methoxyethyl) aminoacetonitrile, N,N-bis[2-(methoxymethoxy)ethyl] aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]

aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

The basic compound is preferably formulated in an amount of 0.001 to 10 parts, and especially 0.01 to 1 part, per part of the photoacid generator. Less than 0.001 part of the basic compound may fail to achieve the desired effects thereof, while the use of more than 10 parts would result in too low a sensitivity and resolution.

Other Components

In the resist composition, a compound bearing a ≡C—COOH group in a molecule may be blended. Exemplary, non-limiting compounds bearing a ≡C—COOH group include one or more compounds selected from Groups I and II below. Including this compound improves the PED stability of the resist and ameliorates edge roughness on nitride film substrates.

Group I:

Compounds in which some or all of the hydrogen atoms on the phenolic hydroxyl groups of the compounds of general formulas (A1) to (A10) below have been replaced with —$R^{401}$—COOH (wherein $R^{401}$ is a straight or branched alkylene of 1 to 10 carbon atoms), and in which the molar ratio C/(C+D) of phenolic hydroxyl groups (C) to ≡C—COOH groups (D) in the molecule is from 0.1 to 1.0.

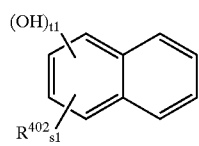

A1

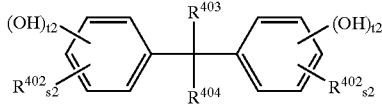

A2

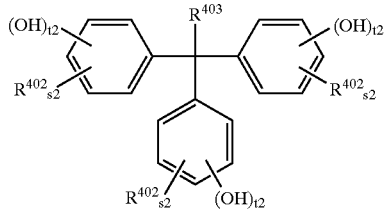

A3

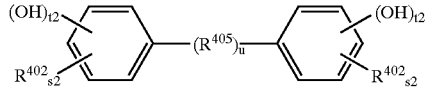

A4

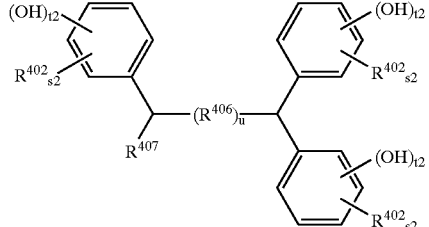

A5

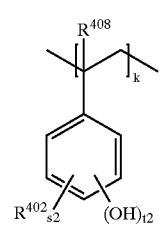

A6

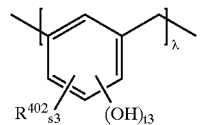

A7

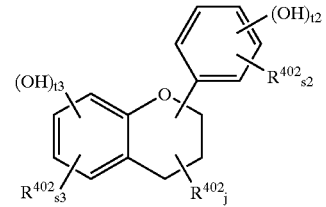

A8

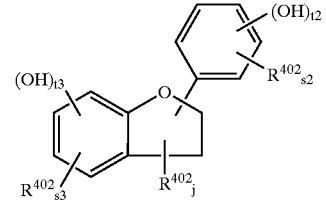

A9

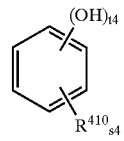

A10

In these formulas, $R^{408}$ is hydrogen or methyl; $R^{402}$ and $R^{403}$ are each hydrogen or a straight or branched alkyl or alkenyl of 1 to 8 carbon atoms; $R^{404}$ is hydrogen, a straight or branched alkyl or alkenyl of 1 to 8 carbon atoms, or a —$(R^{409})_h$—COOR' group (R' being hydrogen or —$R^{409}$—

COOH); $R^{405}$ is —$(CH_2)_i$— (wherein i is 2 to 10), an arylene of 6 to 10 carbon atoms, carbonyl, sulfonyl, an oxygen atom, or a sulfur atom; $R^{406}$ is an alkylene of 1 to 10 carbon atoms, an arylene of 6 to 10 carbon atoms, carbonyl, sulfonyl, an oxygen atom, or a sulfur atom; $R^{407}$ is hydrogen, a straight or branched alkyl or alkenyl of 1 to 8 carbon atoms, or a hydroxyl-substituted phenyl or naphthyl; $R^{409}$ is a straight or branched alkylene of 1 to 10 carbon atoms; $R^{410}$ is hydrogen, a straight or branched alkyl or alkenyl of 1 to 8 carbon atoms, or a —$R^{411}$—COOH group; $R^{411}$ is a straight or branched alkylene of 1 to 10 carbon atoms; the letter j is an integer from 0 to 5; u and h are each 0 or 1; s1, t1, s2, t2, s3, t3, s4, and t4 are each numbers which satisfy s1+t1=8, s2+t2=5, s3+t3=4, and s4+t4=6, and are such that each phenyl skeleton has at least one hydroxyl group; κ is a number such that the compound of formula (A6) may have a weight average molecular weight of 1,000 to 5,000; and λ is a number such that the compound of formula (A7) may have a weight average molecular weight of 1,000 to 10,000.

Group II:
Compounds of general formulas (A11) to (A15) below.

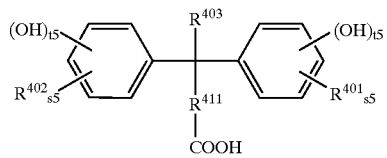

A11

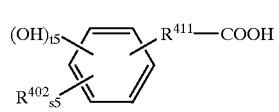

A12

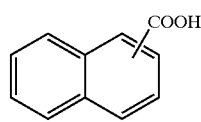

A13

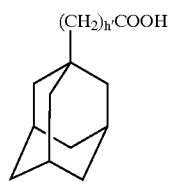

A14

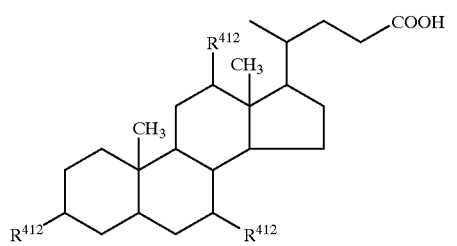

A15

In these formulas, $R^{402}$, $R^{403}$ and $R^{411}$ are as defined above; $R^{412}$ is hydrogen or hydroxyl; s5 and t5 are numbers which satisfy s5≧0, t5≧0, and s5+t5=5; and h' is equal to 0 or 1.

Illustrative, non-limiting examples of the compound bearing a ≡C—COOH group include compounds of the general formulas AI-1 to AI-14 and AII-1 to AII-10 below.

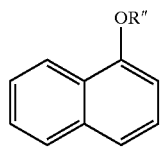

AI-1

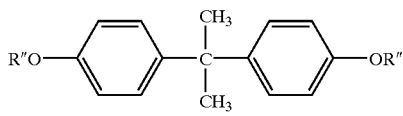

AI-2

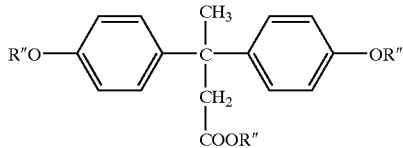

AI-3

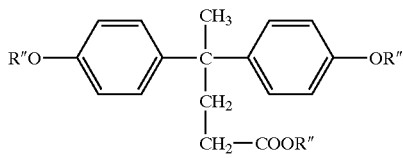

AI-4

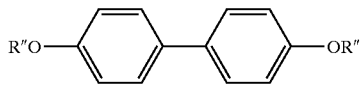

AI-5

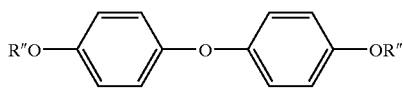

AI-6

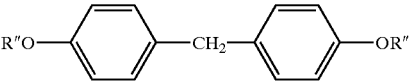

AI-7

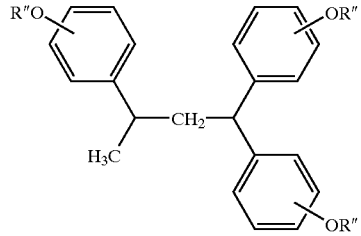

AI-8

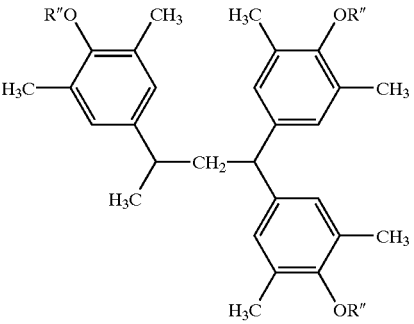

AI-9

In the above formulas, R″ is hydrogen or a CH₂COOH group such that the CH₂COOH group accounts for 10 to 100 mol % of R″ in each compound, α and κ are as defined above.

The compound bearing a ≡C—COOH group within the molecule may be used singly or as combinations of two or more thereof.

The compound bearing a ≡C—COOH group within the molecule is added in an amount ranging from 0 to 5 parts, preferably 0.1 to 5 parts, more preferably 0.1 to 3 parts, further preferably 0.1 to 2 parts, per 100 parts of the base resin. More than 5 parts of the compound can reduce the resolution of the resist composition.

The resist composition of the invention may additionally include an acetylene alcohol derivative for the purpose of enhancing the shelf stability. Preferred acetylene alcohol derivatives are those having the general formula (S1) or (S2) below.

S1

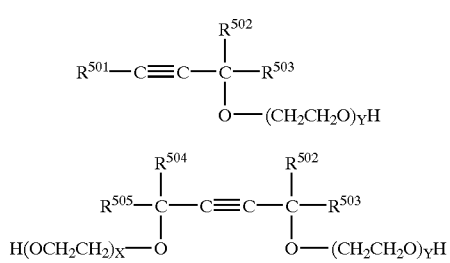

S2

In the formulas, $R^{501}$, $R^{502}$, $R^{503}$, $R^{504}$, and $R^{505}$ are each hydrogen or a straight, branched, or cyclic alkyl of 1 to 8 carbon atoms; and X and Y are each 0 or a positive number, satisfying $0 \leq X \leq 30$, $0 \leq Y \leq 30$, and $0 \leq X+Y \leq 40$.

Preferable examples of the acetylene alcohol derivative include Surfynol 61, Surfynol 82, Surfynol 104, Surfynol 104E, Surfynol 104H, Surfynol 104A, Surfynol TG, Surfynol PC, Surfynol 440, Surfynol 465, and Surfynol 485 from Air Products and Chemicals Inc., and Surfynol E1004 from Nisshin Chemical Industry K.K.

The acetylene alcohol derivative is preferably added in an amount of 0.01 to 2% by weight, and more preferably 0.02 to 1% by weight, per 100% by weight of the resist composition. Less than 0.01% by weight would be ineffective for improving coating characteristics and shelf stability, whereas more than 2% by weight would result in a resist having a low resolution.

The resist composition of the invention may include optional ingredients, for example, a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Florade FC-430 and FC-431 from Sumitomo 3M, Ltd., Surflon S-141 and S-145, KH-10, KH-20, KH-30 and KH-40 from Asahi Glass Co., Ltd., Unidyne DS-401, DS-403 and DS-451 from Daikin Industry Co., Ltd., Megaface F-8151 from Dai-Nippon Ink & Chemicals, Inc., and X-70-092 and X-70-093 from Shin-Etsu Chemical Co., Ltd. Preferred surfactants are Florade FC-430 from Sumitomo 3M, Ltd., KH-20 and KH-30 from Asahi Glass Co., Ltd., and X-70-093 from Shin-Etsu Chemical Co., Ltd.

Pattern formation using the resist composition of the invention may be carried out by a known lithographic technique. For example, the resist composition is applied onto a substrate such as a silicon wafer by spin coating or the like to form a resist film having a thickness of 0.2 to 2.0 μm, which is then pre-baked on a hot plate at 60 to 150° C. for 1 to 10 minutes, and preferably at 80 to 130° C. for 1 to 5 minutes. A patterning mask having the desired pattern is then placed over the resist film, and the film exposed through the mask to an electron beam or to high-energy radiation such as deep-UV rays, an excimer laser, or x-rays in a dose of about 1 to 200 mJ/cm², and preferably about 5 to 100 mJ/cm², then post-exposure baked (PEB) on a hot plate at 60 to 150° C. for 1 to 5 minutes, and preferably at 80 to 130° C. for 1 to 3 minutes. Finally, development is carried out using as the developer an aqueous alkali solution, such as a 0.1 to 5% (preferably 2 to 3%) aqueous solution of tetramethylammonium hydroxide (TMAH), this being done by a conventional method such as dipping, puddling, or spraying for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV rays having a wavelength of 248 to 193 nm, an excimer laser, x-rays, or an electron beam. The desired pattern may not be obtainable outside the upper and lower limits of the above range.

The resist composition comprising the inventive polymer as a base resin lends itself to micropatterning with electron beams or deep-UV rays since it is sensitive to high-energy radiation and has excellent sensitivity, resolution, and etching resistance. Especially because of the minimized absorption at the exposure wavelength of an ArF or KrF excimer laser, a finely defined pattern having sidewalls perpendicular to the substrate can easily be formed.

EXAMPLE

Synthesis Examples and Examples are given below by way of illustration and not by way of limitation. The abbreviation Mw is a weight average molecular weight as measured by GPC using a polystyrene standard, and SEM is scanning electron microscope.

Synthesis Example 1

Epoxy compounds within the scope of the invention were synthesized by the following procedure.

Synthesis Example 1-1

Synthesis of spiro[7-oxa-5-norbornene-2,3'-succinic anhydride] (Monomer 1)

An autoclave was charged with 250 g of itaconic anhydride and 750 g of furan, which were reacted at 30° C. for 48 hours. An excess of furan was distilled off through an evaporator, obtaining crude spiro[7-oxa-5-norbornene-2,3'-succinic anhydride]. Recrystallization from a solvent mixture of hexane and diethyl ether gave 253 g (yield 63%) of spiro[7-oxa-5-norbornene-2,3'-succinic anhydride].

$^1$H-NMR (300 MHz in CDCl$_3$, exo form: endo form=5:5): δ=1.52 (0.5H, d), 1.98–2.06 (1H, m), 2.65 (0.5H, dd), 2.76 (1H, s), 3.12 (1H, q), 4.83 (0.5H, m), 5.09 (0.5H, m), 5.14–5.23 (1H, m), 6.33 (0.5H, dd), 6.50 (0.5H, dd), 6.63 (0.5H, dd), 6.68 (0.5H, dd) ppm.

Synthesis Example 1-2

Synthesis of spiro[7-oxa-5-norbornene-2,4'-tetrahydrofuran-2'-one] (Monomer 2)

To a mixture of 7.6 g of sodium boron hydride, 60 g of water and 180 g of tetrahydrofuran, 18.0 g of spiro[7-oxa-5-norbornene-2,3'-succinic anhydride] was added at 10° C. over one hour. After one hour of stirring, 50 g of 20% hydrochloric acid was added to the reaction solution to stop reaction, followed by another one hour of stirring. The reaction solution was extracted with ethyl acetate. The resulting organic layer was washed with an aqueous saturated sodium hydrogen carbonate solution and then an aqueous saturated sodium chloride solution, dried over anhydrous sodium sulfate, and concentrated in vacuum. The concentrate was purified by vacuum distillation, obtaining 11.8 g (yield 71%) of spiro[7-oxa-5-norbornene-2,4'-tetrahydrofuran-2'-one] (boiling point: 118–120° C./56 Pa).

IR (thin film): ν=3079, 2985, 2948, 2904, 1778, 1673, 1417, 1317, 1272, 1168, 1008, 985, 892, 863, 705 cm$^{-1}$.

$^1$H-NMR of main isomer (300 MHz in CDCl$_3$): δ=1.44 (1H, dd), 1.98 (1H, ddd), 2.33 (1H, dt), 2.68 (1H, q), 3.98 (1H, s), 4.35 (1H, dt), 4.65 (1H, dd), 5.01 (1H, dd), 6.39 (1H, dd), 6.54 (1H, dd) ppm.

Synthesis Example 1-3

Synthesis of spiro[7-oxa-5-norbornene-2,3'-(5',5'-dimethyl)tetrahydrofuran-2'-one] (Monomer 3) and spiro[7-oxa-5-norbornene-2,4'-(5',5'-dimethyl) tetrahydrofuran-2'-one] (Monomer 4)

In a nitrogen atmosphere, 18.0 g of spiro[7-oxa-5-norbornene-2,3'-succinic anhydride] was added to 100 ml of a tetrahydrofuran solution of 2.0M methyl magnesium chloride at 20° C. over one hour. After two hours of stirring, 50 g of 20% hydrochloric acid was added to the reaction solution to stop reaction, followed by another one hour of stirring. After separation of the reaction solution, the resulting organic layer was washed with an aqueous saturated sodium hydrogen carbonate solution and then an aqueous saturated sodium chloride solution, dried over anhydrous sodium sulfate, and concentrated in vacuum. The concentrate was purified and separated by silica gel chromatography, obtaining 6.2 g (yield 32%) of spiro[7-oxa-5-norbornene-2,3'-(5',5'-dimethyl)tetrahydrofuran-2'-one] and 8.3 g (yield 43%) of spiro[7-oxa-5-norbornene-2,4'-(5',5'-dimethyl)tetrahydrofuran-2'-one].

Spectral data of Monomer 4

IR (thin film): ν=2991, 2958, 1772, 1388, 1378, 1322, 1268, 1238, 1207, 1184, 1166, 1130, 1105, 1049, 1008, 962, 943, 916 cm$^{-1}$.

$^1$H-NMR of main isomer (300 MHz in CDCl$_3$): δ=1.30 (1H, dd), 1.40 (3H, s), 1.47 (3H, s), 2.07 (1H, dd), 2.26 (1H, d), 2.58 (1H, d), 4.88 (1H, m), 4.94 (1H, m), 6.41 (1H, dd), 6.54 (1H, dd) ppm.

Synthesis Example 1-4

Synthesis of spiro[7-oxa-5-norbornene-2,4'-(2',2'-dimethyl)tetrahydrofuran] (Monomer 5) and spiro [7-oxa-5-norbornene-2,3'-(2',2'-dimethyl) tetrahydrofuran] (Monomer 6)

In a nitrogen atmosphere, 9.7 g of spiro[7-oxa-5-norbornene-2,3'-(5',5'-dimethyl)tetrahydrofuran-2'-one] and 9.7 g of spiro[7-oxa-5-norbornene-2,4'-(5',5'-dimethyl) tetrahydrofuran-2'-one] were added to a mixture of 3.8 g of lithium aluminum hydride and 100 ml of anhydrous tetrahydrofuran at 20° C. over one hour. After 3 hours of stirring, 3.8 g of water was added to the reaction solution to stop reaction. Then 3.8 g of an aqueous 15% sodium hydroxide solution and 11.4 g of water were added to the reaction solution. After filtration, the filtrate was concentrated, obtaining a mixture of crude 5-hydroxymethyl-5-(2-hydroxy-2-methylpropyl)-7-oxa-2-norbornene and crude 5-α-hydroxyisopropyl-5-(2-hydroxyethyl)-7-oxa-2-norbornene. This was dissolved in 100 ml of pyridine. In a nitrogen stream, 22.9 g of p-toluenesulfonyl chloride was added to the solution at 5° C. The solution was stirred for one hour at this temperature and then for 18 hours at room temperature. Thereafter, the solution was heated to a temperature of 50° C. and stirred for 2 hours at the temperature. After cooling, the reaction mixture was poured into aqueous saturated sodium chloride solution and extracted with ethyl acetate. The ethyl acetate solution was washed with dilute hydrochloric acid, water and an aqueous saturated potassium carbonate solution, dried over magnesium sulfate, and concentrated in vacuum. The concentrate was purified by vacuum distillation, obtaining 15.7 g (yield 87%) of an isomer mixture of spiro[7-oxa-5-norbornene-2,4'-(2',2'-dimethyl)tetrahydrofuran] and spiro[7-oxa-5-norbornene-2,3'-(2',2'-dimethyl)tetrahydrofuran] (boiling point 77–78° C./27 Pa).

IR (thin film): ν=3077, 2975, 2873, 1772, 1461, 1380, 1365, 1317, 1222, 1184, 1151, 1066, 1031, 1010, 925, 904, 815 cm$^{-1}$.

$^{13}$C-NMR of main two isomers (75 MHz in CDCl$_3$).

Isomer A: δ=25.82, 26.06, 36.72, 41.54, 54.02, 63.66, 79.14, 80.76, 84.02, 133.14, 137.60 ppm.

Isomer B: δ=23.48, 25.25, 35.11, 35.81, 53.34, 63.13, 78.30, 81.40, 83.37, 135.34, 137.55 ppm.

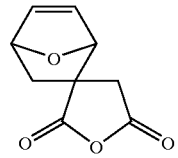

(Monomer 1)

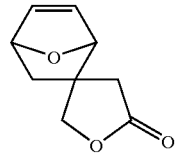

(Monomer 2)

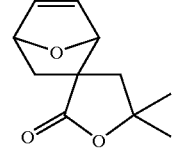

(Monomer 3)

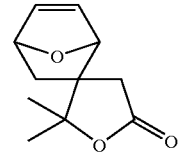

(Monomer 4)

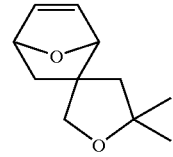

(Monomer 5)

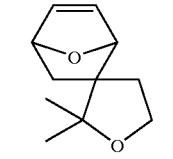

(Monomer 6)

Synthesis Example 2

Polymers within the scope of the invention were synthesized by the following procedure.

Synthesis Example 2-1

Synthesis of Polymer 1

A mixture of 18.0 g of Monomer 1, 104.0 g of 2-ethyl-2-norbornyl 5-norbornene-2-carboxylate, 49.0 g of maleic anhydride, and 18.5 g of 1,4-dioxane was heated at 60° C. To the solution was added 7.4 g of 2,2'-azobis(2,4-dimethylvaleronitrile). The solution was stirred for 15 hours while keeping at 60° C. The reaction solution was cooled to room temperature and dissolved in 500 ml of acetone, which with vigorous stirring, was added dropwise to 10 liters of isopropyl alcohol. The resulting solids were collected by filtration and dried in vacuum at 40° C. for 15 hours, obtaining a polymer, designated Polymer 1, in white powder solid form. The amount was 65.0 g with a yield of 38%.

Synthesis Examples 2-2 to 2-8

Synthesis of Polymers 2-8

Polymers 2 to 8 were synthesized by the same procedure as above or a well-known procedure.

(Polymer 1)

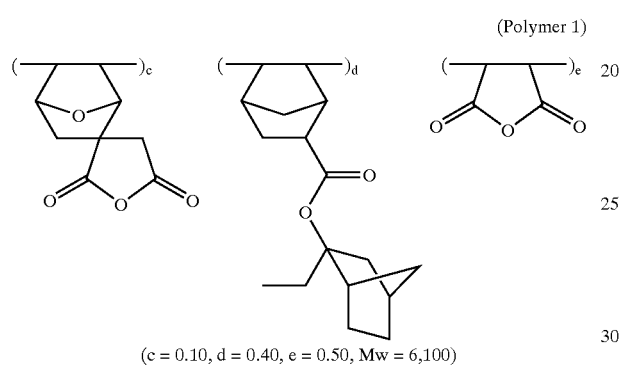

(c = 0.10, d = 0.40, e = 0.50, Mw = 6,100)

(Polymer 2)

(c = 0.10, d = 0.40, e = 0.50, Mw = 7,100)

(Polymer 3)

(c = 0.10, d = 0.40, e = 0.50, Mw = 7,500)

(Polymer 4)

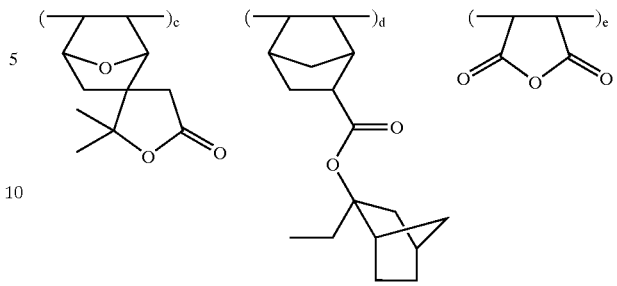

(c = 0.10, d = 0.40, e = 0.50, Mw = 7,300)

(Polymer 5)

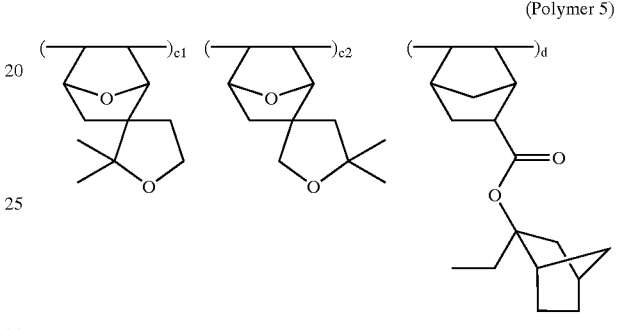

(c1 + c2 = 0.10, d = 0.40, e = 0.50, Mw = 8,600)

(Polymer 6)

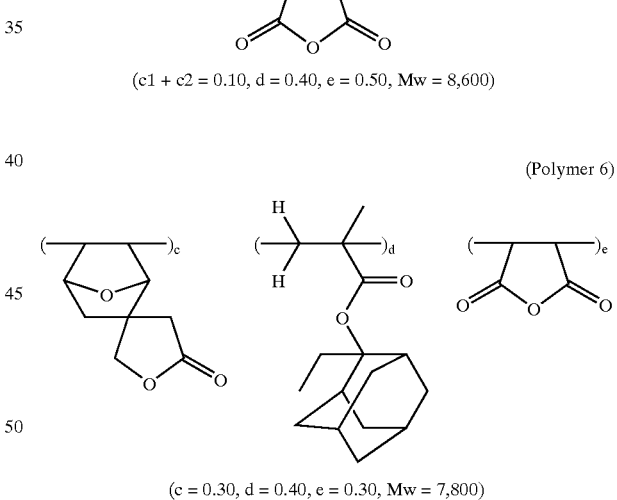

(c = 0.30, d = 0.40, e = 0.30, Mw = 7,800)

(Polymer 7)

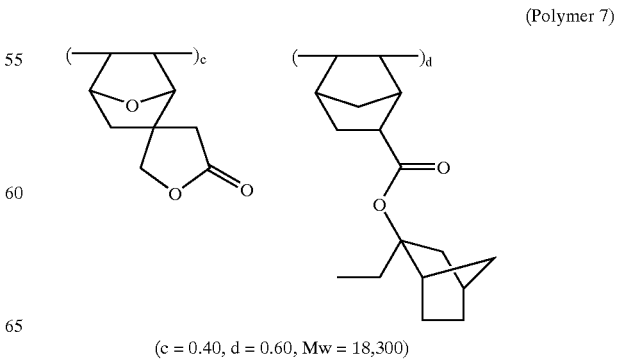

(c = 0.40, d = 0.60, Mw = 18,300)

-continued (Polymer 8)

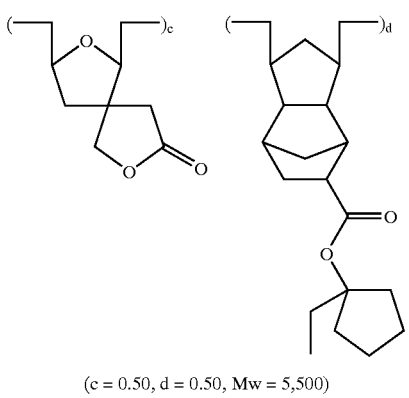

(c = 0.50, d = 0.50, Mw = 5,500)

Example 1

Resist compositions were formulated using the inventive polymers as a base resin and examined for substrate adhesion.

Examples 1-1 to 1-8 & Comparative Examples 1-1, 1-2

Resist compositions were prepared by blending the inventive polymers (Polymers 1 to 8) and comparative polymers (Polymers 9 and 10 shown below) as a base resin, a photoacid generator, a basic compound and a solvent in accordance with the formulation shown in Table 1. They were passed through a Teflon™ filter having a pore diameter of 0.2 μm, obtaining resist solutions.

(Polymer 9)

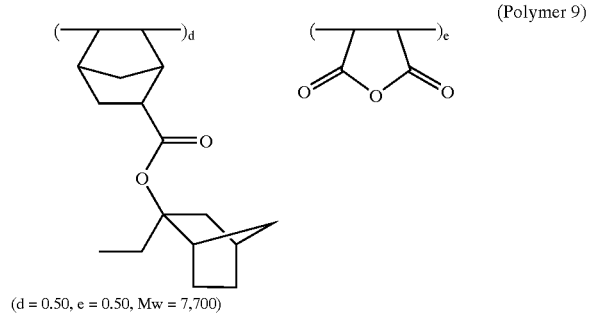

(d = 0.50, e = 0.50, Mw = 7,700)

(Polymer 10)

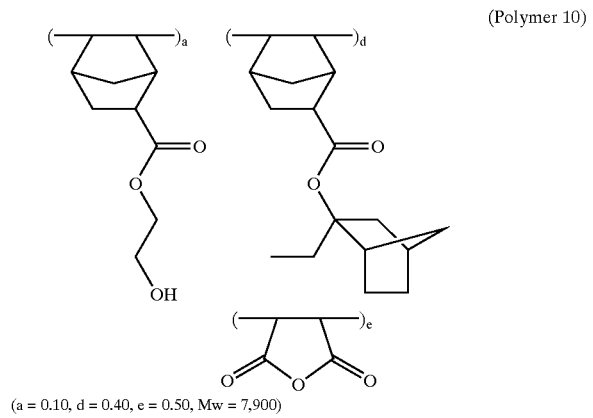

(a = 0.10, d = 0.40, e = 0.50, Mw = 7,900)

These resist solutions were spin coated onto silicon wafers having hexamethyldisilazane spray coated thereon at 90° C. for 40 seconds, then heat treated at 110° C. for 90 seconds to give resist films having a thickness of 0.5 μm. The resist films were exposed using an KrF excimer laser stepper (Nikon Corporation; NA 0.5), then heat treated at 110° C. for 90 seconds, and puddle developed with a solution of 2.38% tetramethylammonium hydroxide in water for 60 seconds, thereby giving 1:1 line-and-space patterns. The wafers as developed were observed under overhead SEM. The minimum width (μm) of lines left unstripped is the limit of adhesion of the resist under test.

The composition and test results of the resist materials are shown in Table 1.

The photoacid generator, basic compound and solvent used are shown below. It is noted that the solvent contained 0.01% by weight of surfactant Florade FC-430 (Sumitomo 3M).

TABLE 1

|  | Resin (pbw) | Photoacid generator (pbw) | Basic compound (pbw) | Solvent (pbw) | Limit of adhesion, μm |
|---|---|---|---|---|---|
| Example 1-1 | Polymer 1 (80) | TPSNf (1.090) | TMMEA (0.236) | PGMEA (480) | 0.28 |
| Example 1-2 | Polymer 2 (80) | TPSNf (1.090) | TMMEA (0.236) | PGMEA (480) | 0.23 |
| Example 1-3 | Polymer 3 (80) | TPSNf (1.090) | TMMEA (0.236) | PGMEA (480) | 0.26 |
| Example 1-4 | Polymer 4 (80) | TPSNf (1.090) | TMMEA (0.236) | PGMEA (480) | 0.26 |
| Example 1-5 | Polymer 5 (80) | TPSNf (1.090) | TMMEA (0.236) | PGMEA (480) | 0.25 |
| Example 1-6 | Polymer 6 (80) | TPSNf (1.090) | TMMEA (0.236) | PGMEA (480) | 0.18 |
| Example 1-7 | Polymer 7 (80) | TPSNf (1.090) | TMMEA (0.236) | PGMEA (480) | 0.20 |
| Example 1-8 | Polymer 8 (80) | TPSNf (1.090) | TMMEA (0.236) | PGMEA (480) | 0.20 |
| Comparative Example 1-1 | Polymer 9 (80) | TPSNf (1.090) | TMMEA (0.236) | PGMEA (480) | >0.50 |
| Comparative Example 1-2 | Polymer 10 (80) | TPSNf (1.090) | TMMEA (0.236) | PGMEA (480) | >0.50 |

TPSNf: triphenylsulfonium nonafluorobutanesulfonate
TMMEA: trismethoxymethoxyethylamine
PGMEA: propylene glycol methyl ether acetate It is evident from Table 1 that the polymers within the scope of the invention have good substrate adhesion.

Example 2

Resist compositions were formulated using the inventive polymers as a base resin and examined for swell-suppressing effect.

Examples 2-1 to 2-8 & Comparative Examples 2-1, 2-2

Resist compositions were prepared by blending the inventive polymers (Polymers 1 to 8) and comparative polymers (Polymers 9 and 10) as a base resin, a photoacid generator, a basic compound and a solvent in accordance with the formulation shown in Table 2. They were passed through a Teflon filter having a pore diameter of 0.2 μm, obtaining resist solutions.

Each resist solution was spin coated on a silicon wafer having hexamethyldisilazane sprayed thereon at 90° C. for 90 seconds and heat treated at 110° C. for 90 seconds, forming a resist film of 0.5 μm thick. Using a KrF excimer laser stepper (Nikon Corp., NA=0.5), the resist film was exposed to light in total eleven spots at different exposures including five points spaced apart from a previously measured sensitivity (Eth, mJ/cm$^2$) at a pitch of 5% in each of descending and ascending directions. Thereafter, the resist film was heat treated at 110° C. for 90 seconds, at which point of time the thickness of the film at different exposure spots was measured. It is a film thickness (Å) before development. The coated silicon wafer was immersed in a 2.38% tetramethylammonium hydroxide aqueous solution for 200 seconds for development, at which point of time the thickness of the film at different exposure spots was measured. It is a film thickness (Å) after development. For each of the different exposure spots, the film thicknesses before and after development were compared. The spot where a film thickness increase after development was observed was regarded as having been swollen, with the maximum of thickness increase being reported as a swell (Å).

The formulation and test results of the resist compositions are shown in Table 2.

The photoacid generator, basic compound and solvent used are shown below. It is noted that the solvent contained 0.01% by weight of surfactant Florade FC-430 (Sumitomo 3M).

TABLE 2

|  | Resin (pbw) | Photoacid generator (pbw) | Basic compound (pbw) | Solvent (pbw) | Swell, Å |
|---|---|---|---|---|---|
| Example 2-1 | Polymer 1 (80) | TPSNf (1.090) | TMMEA (0.236) | PGMEA (480) | −57 |
| Example 2-2 | Polymer 2 (80) | TPSNf (1.090) | TMMEA (0.236) | PGMEA (480) | −49 |
| Example 2-3 | Polymer 3 (80) | TPSNf (1.090) | TMMEA (0.236) | PGMEA (480) | −31 |
| Example 2-4 | Polymer 4 (80) | TPSNf (1.090) | TMMEA (0.236) | PGMEA (480) | −32 |
| Example 2-5 | Polymer 5 (80) | TPSNf (1.090) | TMMEA (0.236) | PGMEA (480) | −23 |
| Example 2-6 | Polymer 6 (80) | TPSNf (1.090) | TMMEA (0.236) | PGMEA (480) | −15 |
| Example 2-7 | Polymer 7 (80) | TPSNf (1.090) | TMMEA (0.236) | PGMEA (480) | −33 |
| Example 2-8 | Polymer 8 (80) | TPSNf (1.090) | TMMEA (0.236) | PGMEA (480) | −41 |
| Comparative Example 2-1 | Polymer 9 (80) | TPSNf (1.090) | TMMEA (0.236) | PGMEA (480) | 181 |
| Comparative Example 2-2 | Polymer 10 (80) | TPSNf (1.090) | TMMEA (0.236) | PGMEA (480) | 89 |

TPSNf: triphenylsulfonium nonafluorobutanesulfonate
TMMEA: trismethoxymethoxyethylamine
PGMEA: propylene glycol methyl ether acetate It is evident from Table 2 that the inventive polymers are highly effective for suppressing swell.

Example 3

Resist compositions were formulated using inventive polymers and examined for resolution upon ArF excimer laser exposure.

Examples 3-1 to 3-8

Evaluation of Resist Resolution

Resist compositions were prepared by dissolving Polymers 1 to 8 as the base resin, a photoacid generator, and a basic compound in a solvent in accordance with the formulation shown in Table 3. These compositions were each filtered through a Teflon filter (pore diameter 0.2 μm), thereby giving resist solutions.

These resist solutions were spin-coated onto silicon wafers having an anti-reflection film (ARC25 by Nissan Chemical Co., Ltd., 77 nm) coated thereon, then heat treated at 110° C. for 60 seconds to give resist films having a thickness of 375 nm. The resist films were exposed using an ArF excimer laser stepper (Nikon Corporation; NA 0.55), then heat treated at 110° C. for 60 seconds, and puddle developed with a solution of 2.38% TMAH in water for 60 seconds, thereby giving 1:1 line-and-space patterns. The developed wafers were cut, and the cross section was observed under a sectional SEM. The optimum dose (Eop, mJ/cm$^2$) was defined as the dose which provided a 1:1 resolution at the top and bottom of a 0.20 μm line-and-space pattern. The resolution of the resist under evaluation was defined as the minimum line width (μm) of the lines and spaces that separated at this dose. The shape of the resist pattern was classified into rectangular, rounded head, T-top, forward taper or reverse taper.

The composition and test results of the resist materials are shown in Table 3.

The photoacid generator, basic compound and solvent used are shown below. It is noted that the solvent contained 0.01% by weight of surfactant Florade FC-430 (Sumitomo 3M).

TABLE 3

|  | Resin (pbw) | Photoacid generator (pbw) | Basic compound (pbw) | Solvent (pbw) | Eop, mJ/cm$^2$ | Resolution, μm | Shape |
|---|---|---|---|---|---|---|---|
| Example 3-1 | Polymer 1 (80) | TPSNf (1.090) | TMMEA (0.236) | PGMEA (480) | 28.0 | 0.16 | rectangular |
| Example 3-2 | Polymer 2 (80) | TPSNf (1.090) | TMMEA (0.236) | PGMEA (480) | 30.0 | 0.16 | rectangular |
| Example 3-3 | Polymer 3 (80) | TPSNf (1.090) | TMMEA (0.236) | PGMEA (480) | 29.0 | 0.16 | rectangular |
| Example 3-4 | Polymer 4 (80) | TPSNf (1.090) | TMMEA (0.236) | PGMEA (480) | 28.0 | 0.16 | rectangular |
| Example 3-5 | Polymer 5 (80) | TPSNf (1.090) | TMMEA (0.236) | PGMEA (480) | 29.0 | 0.16 | rectangular |
| Example 3-6 | Polymer 6 (80) | TPSNf (1.090) | TMMEA (0.236) | PGMEA (480) | 32.0 | 0.15 | rectangular |

TABLE 3-continued

| | Resin (pbw) | Photoacid generator (pbw) | Basic compound (pbw) | Solvent (pbw) | Eop, mJ/cm$^2$ | Resolution, µm | Shape |
|---|---|---|---|---|---|---|---|
| Example 3-7 | Polymer 7 (80) | TPSNf (1.090) | TMMEA (0.236) | PGMEA (480) | 24.0 | 0.16 | rectangular |
| Example 3-8 | Polymer 8 (80) | TPSNf (1.090) | TMMEA (0.236) | PGMEA (480) | 27.0 | 0.17 | rectangular |

TPSNf: triphenylsulfonium nonafluorobutanesulfonate
TMMEA: trismethoxymethoxyethylamine
PGMEA: propylene glycol methyl ether acetate It is seen from Table 3 that the resist compositions within the scope of the invention have a high sensitivity and resolution upon ArF excimer laser exposure.

Japanese Patent Application No. 2001-179593 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A compound having the following formula (1):

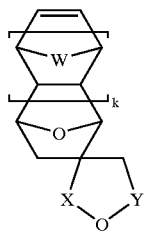

(1)

wherein W is CH$_2$, an oxygen atom or sulfur atom, X and Y are independently —CR$^1$R$^2$—, k is 0 or 1, R$^1$ and R$^2$ are independently hydrogen or straight, branched or cyclic alkyl groups of 1 to 10 carbon atoms in which some or all of the hydrogen atoms on constituent carbon atoms may be substituted with halogen atoms, or R$^1$ and R$^2$, taken together, may form an aliphatic hydrocarbon ring with the carbon atom to which they are connected.

2. The compound of claim 1 having the following formula (2):

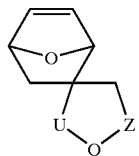

(2)

wherein one of U and Z is —CR$^3$R$^4$—, the other is CH$_2$, R$^3$ and R$^4$ are independently hydrogen or straight, branched or cyclic alkyl groups of 1 to 6 carbon atoms, or R$^3$ and R$^4$, taken together, may form an aliphatic hydrocarbon ring with the carbon atom to which they are connected.

3. A polymer comprising recurring units obtained by polymerizing a compound of claim 2.

4. A resist composition comprising a polymer of claim 3 as a base resin.

5. A process for forming a resist pattern comprising the steps of:

applying the resist composition of claim 4 onto a substrate to form a coating, heat treating the coating and then exposing it to high-energy radiation or electron beam through a photo mask, and optionally heat treating the exposed coating and developing it with a developer.

6. A polymer comprising recurring units obtained by polymerizing a compound of claim 1.

7. A resist composition comprising the polymer of claim 6 as a base resin.

8. A process for forming a resist pattern comprising the steps of:

applying the resist composition of claim 7 onto a substrate to form a coating, heat treating the coating and then exposing it to high-energy radiation or electron beam through a photo mask, and optionally heat treating the exposed coating and developing it with a developer.

9. A compound of claim 1, which is one of the following compounds:

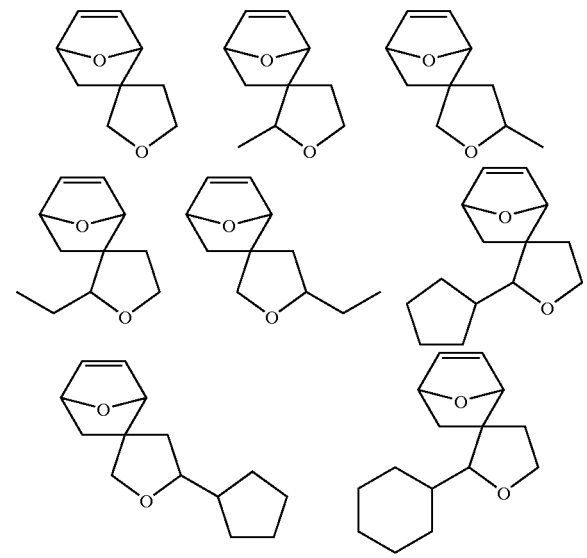

63
-continued

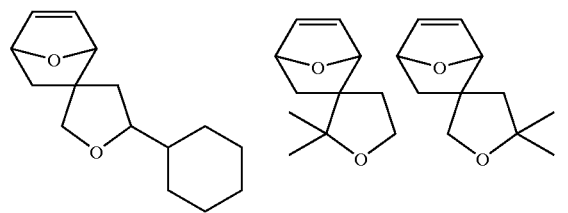
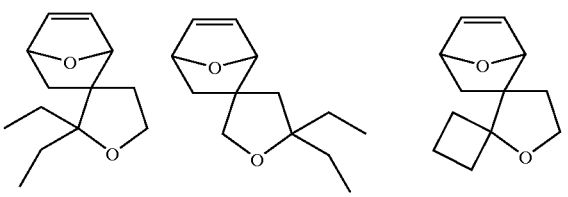
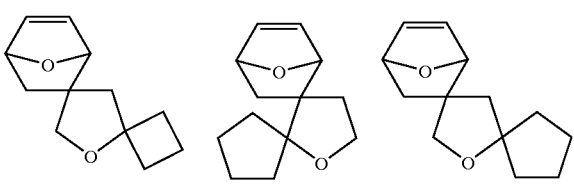
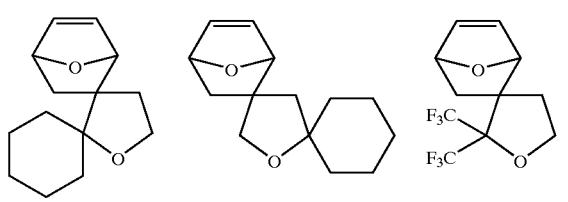
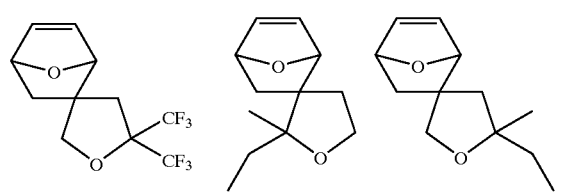
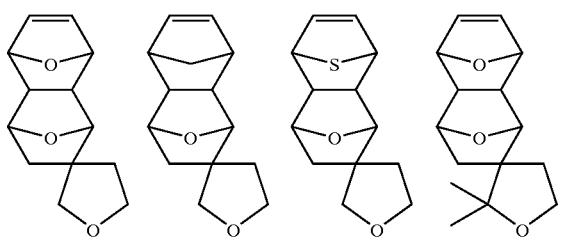
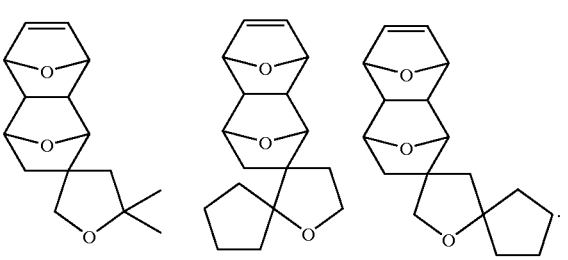

64

10. A polymer comprising:
recurring units from a compound of the formula (1):

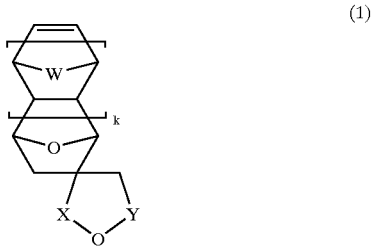

(1)

wherein W is $CH_2$, an oxygen atom or sulfur atom, X and Y are independently —$CR^1R^2$—, k is 0 or 1, $R^1$ and $R^2$ are independently hydrogen or straight, branched or cyclic alkyl groups of 1 to 10 carbon atoms in which some or all of the hydrogen atoms on constituent carbon atoms may be substituted with halogen atoms, or $R^1$ and $R^2$, taken together, may form an aliphatic hydrocarbon ring with the carbon atom to which they are connected;

and recurring units of the following formula (M3):

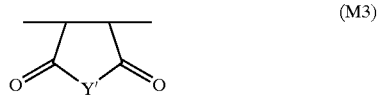

(M3)

wherein Y' is —O— or —($NR^f$)— and $R^f$ is hydrogen or a straight, branched or cyclic alkyl group of 1 to 15 carbon atoms.

11. A polymer of claim 10, wherein at least one recurring unit from a compound of the formula (1) is a recurring unit from a compound of the formula (2):

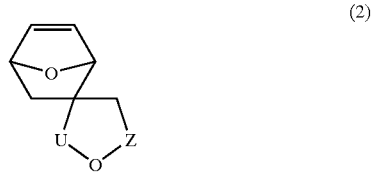

(2)

wherein one of U and Z is —$CR^3R^4$—, the other is $CH_2$, $R^3$ and $R^4$ are independently hydrogen or straight, branched or cyclic alkyl groups of 1 to 6 carbon atoms, or $R^3$ and $R^4$, taken together, may form an aliphatic hydrocarbon ring with the carbon atom to which they are connected.

12. A resist composition comprising a polymer of claim 11 as a base resin.

13. A process for forming a resist pattern comprising the steps of:
applying the resist composition of claim 12 onto a substrate to form a coating,
heat treating the coating and then exposing it to high-energy radiation or electron beam through a photo mask, and
optionally heat treating the exposed coating and developing it with a developer.

14. The polymer of claim 11, wherein the polymer further comprises recurring units of the formula (M1):

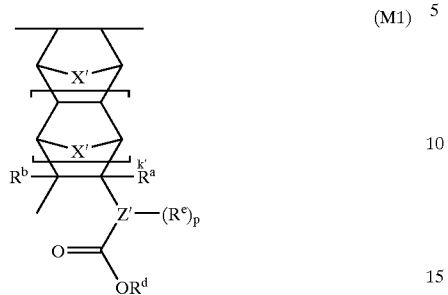

(M1)

wherein $R^a$ is hydrogen, methyl or $CH_2CO_2R^c$, $R^b$ is hydrogen, methyl or $CO_2R^c$, $R^c$ which may be identical or different between $R^a$ and $R^b$ is a straight, branched or cyclic alkyl group of 1 to 15 carbon atoms, $R^d$ is an acid labile group, $R^e$ is a halogen atom, a hydroxyl group, a straight, branched or cyclic alkoxy, acyloxy or alkylsulfonyloxy group having 1 to 15 carbon atoms, or a straight, branched or cyclic alkoxycarbonyloxy or alkoxyalkoxy group having 2 to 15 carbon atoms, in which some or all of the hydrogen atoms on constituent carbon atoms may be substituted with halogen atoms, X' is $CH_2$, an oxygen or sulfur atom, Z' is a single bond or a straight, branched or cyclic (p+2)-valent hydrocarbon group having 1 to 5 carbon atoms, in which at least one methylene group is optionally substituted with an oxygen atom to form a chain ether or cyclic ether or two hydrogen atoms on a common carbon are optionally substituted with an oxygen atom to form a ketone, k' is 0 or 1, p is 0, 1 or 2.

15. A resist composition comprising a polymer of claim 14 as a base resin.

16. A process for forming a resist pattern comprising the steps of:
applying the resist composition of claim 15 onto a substrate to form a coating,
heat treating the coating and then exposing it to high-energy radiation or electron beam through a photo mask, and
optionally heat treating the exposed coating and developing it with a developer.

17. A resist composition comprising a polymer of claim 10 as a base resin.

18. A process for forming a resist pattern comprising the steps of:
applying the resist composition of claim 17 onto a substrate to form a coating,
heat treating the coating and then exposing it to high-energy radiation or electron beam through a photo mask, and
optionally heat treating the exposed coating and developing it with a developer.

19. The polymer of claim 10, wherein the polymer comprises a recurring unit from a compound of the formula (1) which recurring unit is of the formula (1a):

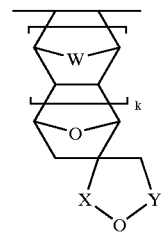

(1a)

wherein W, X, Y and k are as defined for formula (1) above, and
wherein the polymer further comprises recurring units of the formula (M1):

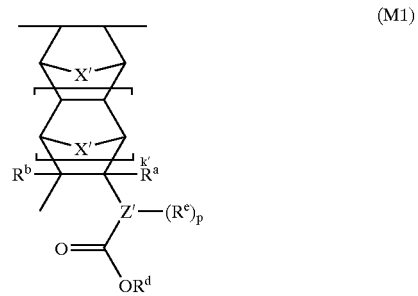

(M1)

wherein $R^a$ is hydrogen, methyl or $CH_2CO_2R^c$, $R^b$ is hydrogen, methyl or $CO_2R^c$, $R^c$ which may be identical or different between $R^a$ and $R^b$ is a straight, branched or cyclic alkyl group of 1 to 15 carbon atoms, $R^d$ is an acid labile group, $R^e$ is a halogen atom, a hydroxyl group, a straight, branched or cyclic alkoxy, acyloxy or alkylsulfonyloxy group having 1 to 15 carbon atoms, or a straight, branched or cyclic alkoxycarbonyloxy or alkoxyalkoxy group having 2 to 15 carbon atoms, in which some or all of the hydrogen atoms on constituent carbon atoms may be substituted with halogen atoms, X' is $CH_2$, an oxygen or sulfur atom, Z' is a single bond or a straight, branched or cyclic (p+2)-valent hydrocarbon group having 1 to 5 carbon atoms, in which at least one methylene group is optionally substituted with an oxygen atom to form a chain ether or cyclic ether or two hydrogen atoms on a common carbon are optionally substituted with an oxygen atom to form a ketone, k' is 0 or 1, p is 0, 1 or 2.

20. A resist composition comprising a polymer of claim 19 as a base resin.

21. A process for forming a resist pattern comprising the steps of:
applying the resist composition of claim 20 onto a substrate to form a coating,
heat treating the coating and then exposing it to high-energy radiation or electron beam through a photo mask, and
optionally heat treating the exposed coating and developing it with a developer.

* * * * *